United States Patent
Kuramochi et al.

(10) Patent No.: US 11,007,774 B2
(45) Date of Patent: May 18, 2021

(54) DROPLET FORMING DEVICE, DROPLET FORMING METHOD, AND DISPENSING APPARATUS

(71) Applicants: Yuzuru Kuramochi, Kanagawa (JP); Daisuke Takagi, Kanagawa (JP); Satoshi Okano, Kanagawa (JP); Takahiko Matsumoto, Kanagawa (JP); Koichi Muramatsu, Kanagawa (JP); Satoshi Nakazawa, Kanagawa (JP); Ryuya Mashiko, Tokyo (JP); Manabu Seo, Kanagawa (JP); Hidekazu Yaginuma, Kanagawa (JP); Mayuko Murano, Kanagawa (JP)

(72) Inventors: Yuzuru Kuramochi, Kanagawa (JP); Daisuke Takagi, Kanagawa (JP); Satoshi Okano, Kanagawa (JP); Takahiko Matsumoto, Kanagawa (JP); Koichi Muramatsu, Kanagawa (JP); Satoshi Nakazawa, Kanagawa (JP); Ryuya Mashiko, Tokyo (JP); Manabu Seo, Kanagawa (JP); Hidekazu Yaginuma, Kanagawa (JP); Mayuko Murano, Kanagawa (JP)

(73) Assignee: Ricoh Company, Ltd., Tokyo (JP)

( * ) Notice: Subject to any disclaimer, the term of this patent is extended or adjusted under 35 U.S.C. 154(b) by 57 days.

(21) Appl. No.: 16/435,779

(22) Filed: Jun. 10, 2019

(65) Prior Publication Data
US 2020/0023328 A1    Jan. 23, 2020

(30) Foreign Application Priority Data

Jul. 20, 2018 (JP) ............................ JP2018-136445
Feb. 20, 2019 (JP) ............................ JP2019-028525

(51) Int. Cl.
*B41J 2/045* (2006.01)
*B41J 2/025* (2006.01)

(52) U.S. Cl.
CPC ........... *B41J 2/04501* (2013.01); *B41J 2/025* (2013.01); *B41J 2/04581* (2013.01); *B41J 2202/15* (2013.01)

(58) Field of Classification Search
CPC .......... B41J 2202/15; B41J 2002/14435; B41J 2/14298; B41J 1/14; B41J 2/04501;
(Continued)

(56) References Cited

U.S. PATENT DOCUMENTS 5,255,016 A * 10/1993 Usui ................... B41J 2/14282
                                                          310/328
2007/0029070 A1    2/2007 Yamamoto et al.
(Continued)

FOREIGN PATENT DOCUMENTS

JP    2002-301433    10/2002
JP    2013-208900    10/2013
(Continued)

OTHER PUBLICATIONS

Extended European Search Report dated Nov. 21, 2019 in European Patent Application No. 19178041.0, 6 pages.

*Primary Examiner* — Henok D Legesse
(74) *Attorney, Agent, or Firm* — Oblon, McClelland, Maier & Neustadt, L.L.P.

(57) ABSTRACT

A droplet forming device is provided. The droplet forming device includes a liquid holder configured to hold a liquid, a film having a discharge hole, two or more vibration generators configured to vibrate the film, and a driver configured to apply a driving signal to the vibration genera-
(Continued)

tors. One or more of the vibration generators are disposed in each region on the film where a polarity of bending moment differs.

15 Claims, 12 Drawing Sheets

(58) Field of Classification Search
CPC .. B41J 2/04581; B41J 2/0456; B41J 2/14201; B41J 2/125
See application file for complete search history.

(56) References Cited

U.S. PATENT DOCUMENTS

| | | |
|---|---|---|
| 2008/0241962 A1 | 10/2008 | Wang |
| 2009/0232685 A1 | 9/2009 | Kamitani et al. |
| 2010/0029014 A1 | 2/2010 | Wang |
| 2011/0229356 A1 | 9/2011 | Kamitani et al. |
| 2016/0175834 A1 | 6/2016 | Seo et al. |
| 2016/0176191 A1* | 6/2016 | Kuramochi ........... B01L 3/0268 347/70 |
| 2018/0169650 A1 | 6/2018 | Somada et al. |

FOREIGN PATENT DOCUMENTS

| | | |
|---|---|---|
| JP | 2016-116489 | 6/2016 |
| JP | 2016-203157 | 12/2016 |
| JP | 2017-209857 | 11/2017 |
| JP | 2017-209980 | 11/2017 |
| JP | 2018-1098 A | 1/2018 |

* cited by examiner

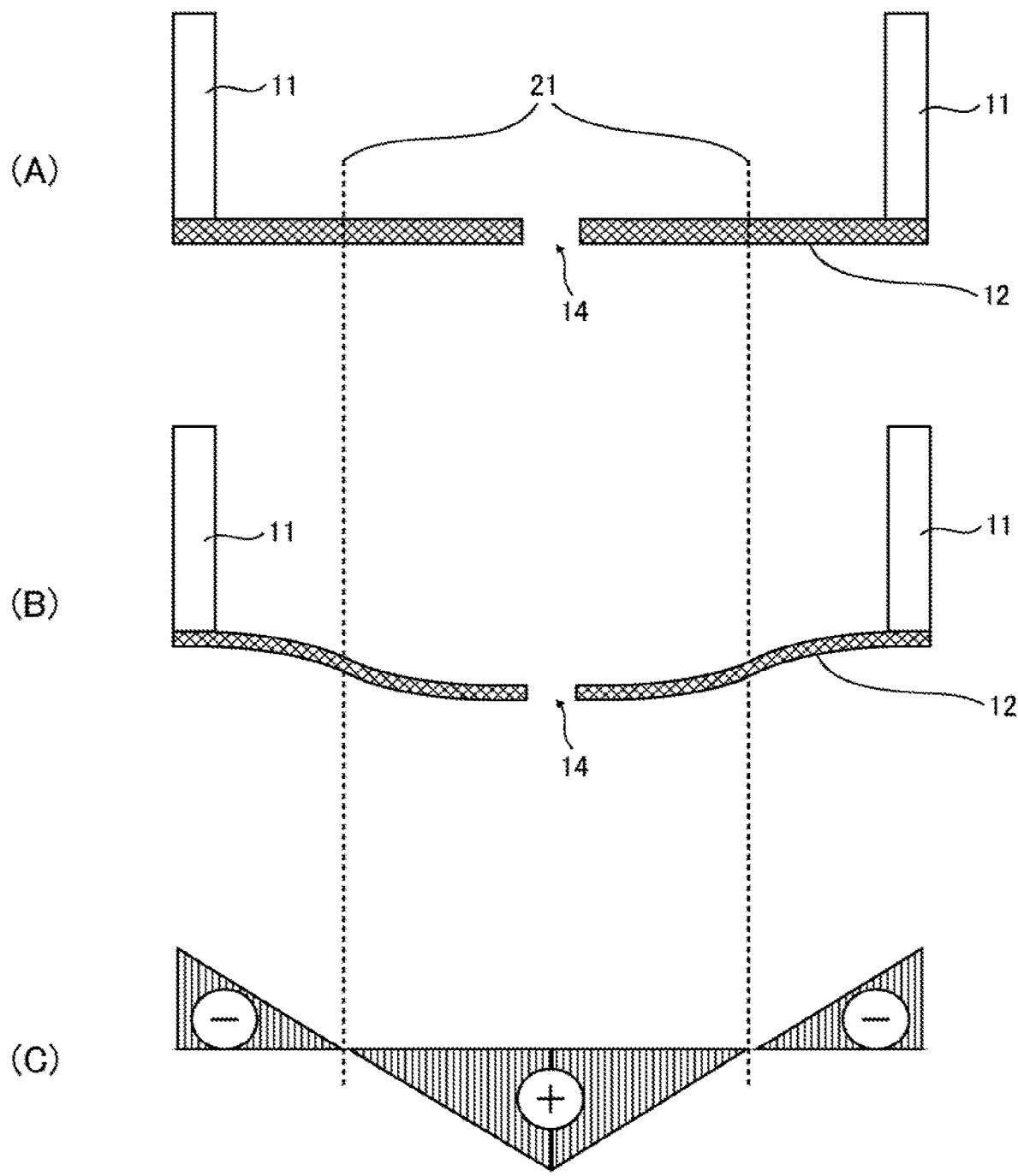

US 11,007,774 B2

DROPLET FORMING DEVICE, DROPLET FORMING METHOD, AND DISPENSING APPARATUS

CROSS-REFERENCE TO RELATED APPLICATIONS

This patent application is based on and claims priority pursuant to 35 U.S.C. § 119(a) to Japanese Patent Application Nos. 2018-136445 and 2019-028525, filed on Jul. 20, 2018 and Feb. 20, 2019, respectively, in the Japan Patent Office, the entire disclosure of each of which is hereby incorporated by reference herein.

BACKGROUND

Technical Field

The present disclosure relates to a droplet forming device, a droplet forming method, and a dispensing apparatus.

Description of the Related Art

In recent years, with the progress of stem cell technologies, techniques for discharging a plurality of cells by inkjet to form tissues have been developed.

Under such circumstances, a droplet forming device for discharging a cell suspension in which cells are dispersed has been proposed. The device is configured to vibrate a film provided with discharge holes by an actuator to discharge a liquid on the film. In this droplet forming device, a liquid holder for holding the liquid is open to the atmosphere, and the liquid on the film can be directly jetted without applying any pressure for discharging droplets in the liquid holder. Therefore, even a high-surface-tension liquid such as a cell suspension can be stably discharged without being affected by air bubbles remaining in the liquid holder.

An inkjet recording head has been proposed having a configuration in which a difference in level is provided between an upper electrode end and a lower electrode end of a piezoelectric film of a piezoelectric element disposed on a film provided with discharge holes, for preventing dielectric breakdown between the upper and lower electrodes in contact with the piezoelectric film and preventing a decrease in drive efficiency due to an increase in rigidity of the piezoelectric film.

SUMMARY

In accordance with some embodiments of the present invention, a droplet forming device is provided. The droplet forming device includes a liquid holder configured to hold a liquid, a film having a discharge hole, two or more vibration generators configured to vibrate the film, and a driver configured to apply a driving signal to the vibration generators. One or more of the vibration generators are disposed in each region on the film where a polarity of bending moment differs.

BRIEF DESCRIPTION OF THE DRAWINGS

A more complete appreciation of the disclosure and many of the attendant advantages thereof will be readily obtained as the same becomes better understood by reference to the following detailed description when considered in connection with the accompanying drawings, wherein:

FIG. 1A is a diagram illustrating a vibration state of the film in an initial stage (A) and during driving (B) and a bending moment (C) of the film;

Figure 1B:
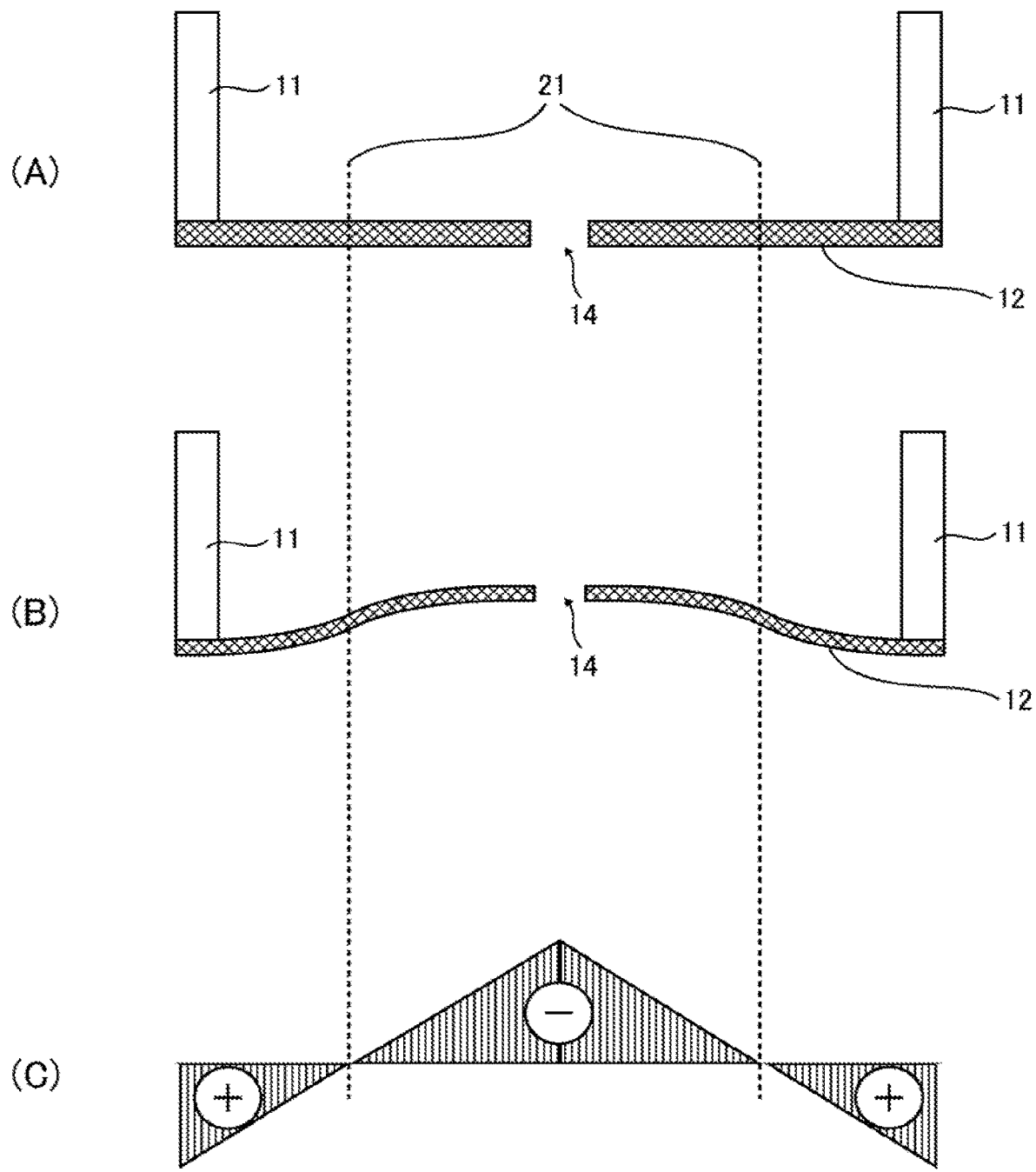
FIG. 1B is a diagram illustrating a vibration state of the film in an initial stage (A) and during driving (B) and a bending moment (C) of the film.

The accompanying drawings are intended to depict example embodiments of the present invention and should not be interpreted to limit the scope thereof. The accompanying drawings are not to be considered as drawn to scale unless explicitly noted.

DETAILED DESCRIPTION

The terminology used herein is for the purpose of describing particular embodiments only and is not intended to be limiting of the present invention. As used herein, the singular forms "a", "an" and "the" are intended to include the plural forms as well, unless the context clearly indicates otherwise. It will be further understood that the terms "includes" and/or "including", when used in this specification, specify the presence of stated features, integers, steps, operations, elements, and/or components, but do not preclude the presence or addition of one or more other features, integers, steps, operations, elements, components, and/or groups thereof.

Embodiments of the present invention are described in detail below with reference to accompanying drawings. In describing embodiments illustrated in the drawings, specific terminology is employed for the sake of clarity. However, the disclosure of this patent specification is not intended to be limited to the specific terminology so selected, and it is to be understood that each specific element includes all technical equivalents that have a similar function, operate in a similar manner, and achieve a similar result.

For the sake of simplicity, the same reference number will be given to identical constituent elements such as parts and materials having the same functions and redundant descriptions thereof omitted unless otherwise stated.

According to an embodiment of the present invention, a droplet forming device that provides sufficient driving force by increasing displacement efficiency of a film and provides high droplet productivity by shortening the period of residual vibration of the film is provided.

Droplet Forming Device and Droplet Forming Method

A droplet forming device according to an embodiment of the present invention includes: a liquid holder configured to hold a liquid; a film having a discharge hole; two or more vibration generators configured to vibrate the film; and a driver configured to apply a driving signal to the vibration generators, where one or more of the vibration generators are disposed in each region on the film where a polarity of bending moment differs.

The droplet forming method according to an embodiment of the present invention forms droplets by using the droplet forming device according to an embodiment of the present invention.

Conventional droplet forming devices form droplets by vibrating a film by a single vibration generator. When a single piezoelectric element is used as a vibration generator, a sufficient driving force for displacing the film cannot be generated (i.e., displacement efficiency of the film is low), since the amount of displacement of the film depends on the maximum driving voltage applicable to the piezoelectric element. On the other hand, when the number of times of droplet formation per unit time is increased, it is necessary to apply an inhibitory signal for inhibiting residual vibration of the film generated after droplet formation. In the case of a single vibration generator, it is necessary to provide an interval time from the end of the output of a discharge signal for forming droplets to the start of the output of the inhibitory signal. Therefore, the period of residual vibration of the film is undesirably prolonged.

In view of this situation, in the droplet forming device according to an embodiment of the present invention that includes: a liquid holder configured to hold a liquid; a film having a discharge hole; two or more vibration generators configured to vibrate the film; and a driver configured to apply a driving signal to the vibration generators, where one or more of the vibration generators are disposed in each region on the film where a polarity of bending moment differs, preferably, the driver is configured to selectively apply an arbitrary driving signal to the two or more vibration generators to control the phase, amplitude, and cycle of vibration generated by each vibration generator, so that a sufficient driving force is provided by increasing displacement efficiency of the film, liquid selectivity is expanded, and droplet productivity is improved by shortening the period of residual vibration of the film.

Specifically, the droplet forming device according to an embodiment of the present invention includes a droplet discharger including the liquid holder, the film, and the vibration generators, and the driver, and optionally other devices as required.

Droplet Discharger

The droplet discharger includes the liquid holder, the film, and the vibration generators, and may further include other members as necessary.

The droplet discharger may be of either open-head or close-head.

Liquid Holder

The liquid holder is a unit configured to hold a liquid.

When the droplet discharger is open-head, an atmospheric opening may be provided on an upper part thereof. The position of the atmospheric opening is not limited to the upper part. The liquid holder is configured such that air bubbles mixed in the liquid can be discharged from the atmospheric opening.

The shape, size, material, and structure of the liquid holder are not particularly limited and can be appropriately selected according to the purpose.

Examples of the material of the liquid holder include, but are not limited to, stainless steel, nickel, aluminum, silicon dioxide, alumina, and zirconia.

Among these, a material having low adhesion to cells or proteins is preferred when handling cells or proteins as particles.

It is generally said that adhesion to cells depends on the contact angle of a material with water. Highly hydrophilic or highly hydrophobic materials have low adhesion to cells. As highly hydrophilic materials, various metal materials and ceramics (metal oxides) may be used. As highly hydrophobic materials, fluororesin may be used.

In addition, adhesion to cells can be reduced by coating the surface of a material with, for example, the metal or metal oxide materials described above or synthetic phospholipid polymers that mimic cell membrane (e.g., LIPIDURE available from NOF CORPORATION).

Film

The film is a member on which a discharge hole (nozzle) is formed, configured to discharge the liquid held in the liquid holder as droplets from the discharge hole by its vibration motion.

The film is fixed to a lower end portion of the liquid holder when the droplet discharger is open-head.

The film is fixed to an upper end portion of the liquid holder when the droplet discharger is close-head.

The liquid held in the liquid holder is discharged as droplets from the discharge hole, which is a through hole, by vibration of the film.

The planar shape, size, material, and structure of the film are not particularly limited and can be appropriately selected according to the purpose.

The planar shape of the film may be, for example, a circle, an ellipse, a rectangle, a square, or a rhombus.

As the material of the film, a material having a certain degree of hardness is preferable, because if the material is too soft, the film is easy to vibrate and difficult to immediately reduce vibration when discharging is suspended. Examples of suitable materials include, but are not limited to, metals, ceramics, and polymer materials. Specific examples thereof include, but are not limited to, stainless steel, nickel, aluminum, silicon dioxide, alumina, and zirconia. Among these, a material having low adhesion to cells or proteins is preferred when handling cells or proteins as particles, as is the case of the liquid holder.

Discharge Hole

The discharge holes are not particularly limited with respect to the number of rows, arrangement form, spacing (pitch), shape and size of the opening, and the like, and can be appropriately selected according to the purpose.

The number of rows of the discharge holes is not particularly limited and can be appropriately selected according to the purpose. Preferably, one or more rows, more preferably from one to four rows, are provided along the longitudinal direction of the discharge surface of the droplet discharger. By providing one or more rows of the discharge holes, the number of droplets discharged per unit time can be increased and different types of particles (e.g., cells) can be discharged from the respective rows at one time.

The number of the discharge holes per row is not particularly limited and may be appropriately selected depending on the purpose, but is preferably from 2 to 100, more preferably from 2 to 50, and much more preferably from 2 to 12. When the number of the discharge holes per row is from 2 to 100, the number of droplets discharged per unit time is increased, thereby providing a droplet forming device having high productivity.

The arrangement form of the discharge holes is not particularly limited and can be appropriately selected according to the purpose and may be either a regular arrangement (e.g., staggered arrangement) or an irregular arrangement.

When the discharge holes are disposed in a plurality of rows, it is preferable that a partition is provided between the rows to prevent interference between droplets discharged from adjacent discharge holes and to improve detection sensitivity of particles. As the partition, for example, a partition plate may be used.

Preferably, the discharge holes are arranged at equal intervals. The interval (pitch) P, which is the shortest distance between the centers of adjacent discharge holes, is not particularly limited and may be appropriately selected according to the purpose, but is preferably from 50 to 1,000 μm.

The shape of the opening of the discharge holes is not particularly limited and may be selected according to the purpose, and may be circular, elliptical, or square.

There average diameter of the discharge holes is not particularly limited and can be appropriately selected according to the purpose. To avoid clogging of the discharge holes with the particles, it is preferable that the average diameter of the discharge holes is twice or more of the particle size.

For example, when the particles are animal cells, particularly human cells generally having a size of from 5 to 50 μm, the average diameter of the discharge holes is preferably from 10 to 100 μm.

On the other hand, when the droplets are too large, it is difficult to achieve the purpose of forming minute droplets. Therefore, the average diameter of the discharge holes is preferably 200 μm or less. Accordingly, the preferred average diameter of the discharge holes is in the range of from 10 to 200 μm.

Vibration Generator

The vibration generator vibrates the film to discharge droplets from the discharge hole (nozzle).

The vibration generator is formed on a lower surface side (discharge surface side) of the film when the droplet discharger is open-head.

The vibration generator is formed on an upper surface side (non-discharge surface side) of the film when the droplet discharger is close-head.

To increase displacement efficiency of the film and shorten the period of residual vibration of the film, two or more vibration generators are provided. Preferably, the number of the vibration generators is from 2 to 10, more preferably from 2 to 5, and particularly preferably 2 for simple installation of the driver and wirings.

Preferably, the two or more vibration generators are disposed on the film spaced outward by a certain distance from the center of the discharge hole, to increase displacement efficiency of the film and shorten the period of residual vibration of the film.

Preferably, the two or more vibration generators are disposed on the film in an annular shape or a frame-like shape with respect to the center of the discharge hole, to increase displacement efficiency of the film and shorten the period of residual vibration of the film.

With respect to the arrangement of the two or more vibration generators, referring to FIGS. 1A and 1B, it is preferable that each of the vibration generators is disposed in each region on a film 12 where the polarity (+/−) of the bending moment differs, i.e., each region on a plus (+) side and a minus (−) side of the film 12 with respect to a bending moment polarity (+/−) conversion line 21 therebetween. This arrangement makes it possible to change the direction of displacement of the film generated by each vibration generator, and therefore to individually drive each vibration generator at appropriate timings. Accordingly, the displacement of the film can be controlled in a manner such that high displacement efficiency and high vibration isolation effect can be achieved.

When the film 12 has a circular shape having a radius of r, preferably, one of the two or more vibration generator is disposed inside a concentric circular region on the film 12 having a radius of approximately (½)r and another one of the vibration generators is disposed outside the concentric circular region. In the present disclosure, a concentric circle having a radius of "approximately" (½)r refers to that existing in the vicinity of a concentric circle having a radius of (½)r, more specifically, a concentric circle existing in a region laid between a concentric circle having a radius of (⅖)r and another concentric circle having a radius of (⅗)r. The bending moment polarity (+/−) conversion line 21 may fluctuate within the above-described range depending on thickness unevenness or material unevenness of the film. The arrangement such that each of the vibration generators is disposed in each region on inside and outside of the bending moment polarity (+/−) conversion line 21 makes it possible to change the direction of displacement of the film 12 generated by each vibration generator and therefore to individually drive each vibration generator at appropriate timings, thereby increasing displacement efficiency of the film and shortening the period of residual vibration of the film.

It is preferable that a driving signal applied to each of the vibration generators is so adjusted that displacement peaks of the film generated by the vibration generators are superimposed with each other. By superimposing displacement peaks of vibrations generated by the vibration generators, higher displacement efficiency of the film can be achieved based on the principle of wave superposition.

It is preferable that a driving signal applied to each of the vibration generators is so adjusted that displacement peaks of residual vibrations of the film generated by the vibration generators are canceled with each other. By superimposing displacement peaks of residual vibrations of the film generated by the vibration generators so as to cancel the displacement peaks, higher vibration isolation effect of the film can be achieved based on the principle of wave superposition.

Preferred examples of the vibration generator include a piezoelectric element. The piezoelectric element may be configured with a piezoelectric material sandwiched between electrodes for applying a voltage to the upper and lower surfaces of the piezoelectric material. In this case, as a voltage is applied from the driver to between the electrodes on the upper and lower surfaces of the piezoelectric element, compressive stress is applied in the lateral direction of the film and the film is vibrated in the vertical direction.

The piezoelectric material is not particularly limited and may be appropriately selected according to the purpose. Examples of the piezoelectric material include, but are not limited to, lead zirconate titanate (PZT), bismuth iron oxide, metal niobate, barium titanate, and these materials to which a metal or a different oxide is added. Among these, lead zirconate titanate (PZT) is preferable.

Driver

The driver is not particularly limited and may be appropriately selected according to the purpose. For example, when the droplet discharger is an inkjet head of a piezoelectric pressure method, the driver may be configured to input a driving voltage to the droplet discharger. In this case, the driver can deform the piezoelectric element to discharge minute droplets. Specific examples of the driver include, but are not limited to, a function generator.

The driver selectively applies an arbitrary driving signal to the two or more vibration generators. As a result, the phase, amplitude, and cycle of the vibration generated by each vibration generator can be controlled so as to increase the amount of displacement of the film and to reduce residual vibration.

Preferably, the driving signal contains a natural frequency of the film. In this case, the droplet forming device excites resonance of the film to achieve high drive efficiency.

Liquid

The liquid is not particularly limited and can be appropriately selected according to the purpose. Examples of the liquid include, but are not limited to, a particle suspension and a high-viscosity ink.

Preferred examples of the particle suspension include a cell suspension.

Droplet

Preferably, the droplet contains a particle.

The number of particles contained in the droplet is preferably 1 or more, and more preferably from 1 to 5.

The diameter of the droplet is not particularly limited and can be appropriately selected according to the purpose, but is preferably from 25 to 150 μm. When the diameter of the droplet is 25 μm or more, the diameter of the particle contained therein becomes appropriate and the number of types of applicable particles increases. When the diameter of the droplet is 150 μm or less, discharge of the droplet becomes stable.

Further, it is preferable that the formula R>3r is satisfied, where R represents the diameter of the droplet and r represents the diameter of the particle. When the formula R>3r is satisfied, the relationship between the particle diameter and the droplet diameter is appropriate, and the accuracy in counting particles is improved without being affected by the relationship between the droplet diameter and the droplet diameter.

The amount of the droplet is not particularly limited and may be appropriately selected depending on the purpose, but is preferably 1,000 pL or less, and more preferably 100 pL or less.

The amount of the droplet can be measured by, for example, determining the size of the droplet from an image of the droplet and calculating the volume thereof.

Examples of the particle contained in the droplet include, but are not limited to, metal particles, inorganic particles, and cells. Among these, cells are preferred.

The cells are not particularly limited and may be appropriately selected according to the purpose. All types of cells are usable regardless of whether the cells are. For example, eukaryotic cells, prokaryotic cells, multicellular organism cells, and unicellular organism cells can be used. Each of these may be used alone or two or more of these may be used in combination.

The eukaryotic cells are not particularly limited and can be appropriately selected according to the purpose. Examples of the eukaryotic cells include, but are not limited to, animal cells, insect cells, plant cells, fungi, algae, and protozoans. Each of these may be used alone or two or more of these may be used in combination. Among these, animal cells and fungi are preferable, and cells of human origin are more preferable.

Adherent cells, including either primary cells directly collected from tissues or organs or cells obtained by subculturing the primary cells directly collected from tissues or organs, may also be used. Examples of the adherent cells include, but are not limited to, differentiated cells and undifferentiated cells.

The differentiated cells are not particularly limited and can be appropriately selected according to the purpose. Examples of the differentiated cells include, but not limited to: hepatocytes that are parenchymal cells of the liver; stellate cells; Kupffer cells; vascular endothelial cells; endothelial cells, such as ductal endothelial cells and corneal endothelial cells; fibroblasts; osteoblasts; osteoclasts; periodontal ligament fibroblasts; epidermal cells, such as epidermal keratinocytes; tracheal epithelial cells; gastrointestinal epithelial cells; cervical epithelial cells; epithelial cells such as corneal epithelial cells; mammary gland cells; pericytes; muscle cells, such as smooth muscle cells and cardiac muscle cells; renal cells; pancreatic islets of Langerhans cells; nerve cells, such as peripheral nerve cells and optic nerve cells; cartilage cells; and bone cells.

The undifferentiated cells are not particularly limited and can be appropriately selected according to the purpose. Examples of the undifferentiated cells include, but not limited to: pluripotent stem cells, such as embryonic stem cells being undifferentiated cells and multipotent mesenchymal stem cells; unipotent stem cells, such as vascular endothelial progenitor cells having a differentiation potential; and iPS cells.

The fungi are not particularly limited and can be appropriately selected according to the purpose. Examples of the fungi include, but are not limited to, molds and yeasts. Each of these may be used alone or two or more of these may be used in combination. Among these, yeasts are preferable because the cell cycle thereof is adjustable and haploid thereof are usable.

The cell cycle refers to a process in which cells (daughter cells) generated by cell division become cells (mother cells) that undergo cell division again to produce new daughter cells.

The yeasts are not particularly limited and can be appropriately selected according to the purpose. Preferred examples of the yeasts include, but are not limited to, a Bar-1 deficient yeast having an increased sensitivity to a pheromone (sex hormone) which controls the cell cycle to the G1 phase. When a Bar-1 deficient yeast is used, the abundance ratio of yeasts whose cell cycle are uncontrolled can be lowered, thereby preventing an increase of the number of specific nucleic acids of the cells accommodated in a container.

The prokaryotic cells are not particularly limited and can be appropriately selected according to the purpose. Examples of the prokaryotic cells include, but are not limited to, eubacteria and archaebacteria. Each of these may be used alone or two or more of these may be used in combination.

Preferably, the cells are dead cells. Dead cells can prevent the occurrence of cell division after sorting.

Preferably, the cells are capable of emitting light when receiving light. When the cells are capable of emitting light when receiving light, the number of cells to land on a landing target object can be controlled with high accuracy.

An optical sensor refers to a passive sensor that acquires the shape and the like of a target cell as image data by collecting visible light (light visible to human eyes) and light having longer wavelengths (one of near-infrared, short-wavelength infrared, and thermal infrared regions) with a lens.

Cells Capable of Emitting Light When Receiving Light

The cells capable of emitting light when receiving light are not particularly limited and can be appropriately selected according to the purpose as long as they can emit light when receiving light. Examples of such cells include, but are not limited to, cells stained with a fluorescent dye, cells expressing a fluorescent protein, and cells labeled with a fluorescently labeled antibody.

The staining site by the fluorescent dye, the expression site of the fluorescent protein, or the labeling site by the fluorescently labeled antibody are not particularly limited and may be present in whole cells, cell nuclei, or cell membranes.

Fluorescent Dye

Examples of the fluorescent dye include, but are not limited to, fluoresceins, azos, rhodamines, coumarins, pyrenes, and cyanines. Each of these may be used alone or two or more of these may be used in combination. Among these, fluoresceins, azos, and rhodamines are preferable, and Eosin, Evans Blue, Trypan Blue, Rhodamine 6G, Rhodamine B, and Rhodamine 123 are more preferable.

As the fluorescent dye, commercially available products can be used, such as Eosin Y (manufactured by FUJIFILM Wako Pure Chemical Corporation), Evans Blue (manufactured by FUJIFILM Wako Pure Chemical Corporation), Trypan Blue (manufactured by FUJIFILM Wako Pure Chemical Corporation), Rhodamine 6G (manufactured by FUJIFILM Wako Pure Chemical Corporation), Rhodamine B (manufactured by FUJIFILM Wako Pure Chemical Corporation), and Rhodamine 123 (manufactured by FUJIFILM Wako Pure Chemical Corporation).

Fluorescent Protein

Examples of the fluorescent protein include, but are not limited to, Sirius, EBFP, ECFP, mTurquoise, TagCFP, AmCyan, mTFP1, MidoriishiCyan, CFP, TurboGFP, AcGFP, TagGFP, Azami-Green, ZsGreen, EmGFP, EGFP, GFP2, HyPer, TagYFP, EYFP, Venus, YFP, PhiYFP, PhiYFP-m, TurboYFP, ZsYellow, mBanana, KusabiraOrange, mOrange, TurboRFP, DsRed-Express, DsRed2, TagRFP, DsRed-Monomer, AsRed2, mStrawberry, TurboFP602, mRFP1, JRed, KillerRed, mCherry, mPlum, PS-CFP, Dendra2, Kaede, EosFP, and KikumeGR. Each of these may be used alone or two or more of these may be used in combination.

Fluorescently Labeled Antibody

The fluorescently labeled antibody is not particularly limited and can be appropriately selected depending on the purpose as long as it is fluorescently labeled. Examples of the fluorescently labeled antibody include, but are not limited to, CD4-FITC and CD8-PE. Each of these may be used alone or two or more of these may be used in combination.

Preferably, the cells carry a specific nucleic acid. The number of cells having a specific nucleic acid is not particularly limited and can be appropriately selected depending on the purpose as long as it is plural.

Specific Nucleic Acid

The specific nucleic acid is not particularly limited and can be appropriately selected according to the purpose. Examples of the specific nucleic acid include, but are not limited to, a base sequence used for an infectious disease test, a nucleic acid which does not exist in nature, a base sequence derived from animal cells, and a base sequence derived from plant cells. Each of these may be used alone or two or more of these may be used in combination. Moreover, a plasmid can also be suitably used as the specific nucleic acid.

The nucleic acid refers to a macromolecular organic compound in which nitrogen-containing bases derived from purines or pyrimidines, sugars, and phosphoric acids are regularly bound.

The specific nucleic acid is not particularly limited and can be appropriately selected according to the purpose. Examples thereof include, but are not limited to, DNA and RNA. Among these, a DNA corresponding to an RNA derived from an infectious disease fixation region such as norovirus and a DNA not existing in nature are suitably used.

The specific nucleic acid in the plurality of cells may be a specific nucleic acid derived from the cell in use or a specific nucleic acid introduced by gene transfer. When the specific nucleic acid is a specific nucleic acid introduced by gene transfer or a plasmid, it is preferable to confirm whether one copy of the specific nucleic acid has been introduced into one cell. The method for confirming whether one copy of the specific nucleic acid has been introduced is not particularly limited and may be appropriately selected according to the purpose. The confirmation can be made by, for example, a sequencer, a PCR method, a Southern blotting method.

The method of gene transfer is not particularly limited and can be appropriately selected according to the purpose as long as the specific nucleic acid sequence can be introduced to the target location with the target number of molecules. Examples thereof include, but are not limited to, homologous recombination, CRISPR/Cas9, TALEN, Zinc finger nuclease, Flip-in, and Jump-in. In particular, in the case of yeast, homologous recombination is preferred for high efficiency and ease of control.

The metal particles are not particularly limited and can be appropriately selected according to the purpose. Examples of the metal particles include, but are not limited to, silver particles and copper particles. In this case, the discharged droplets can be used for drawing wirings.

The inorganic particles are not particularly limited and can be appropriately selected according to the purpose. Examples of the inorganic particles include, but are not limited to, titanium oxide and silicon oxide that are used for white inks and for application of spacer materials.

In a case in which the particles aggregate, the number of the particles in the liquid can be adjusted by adjusting the concentration of the particles in the liquid, since the concentration and number of the particles in the liquid follow the Poisson distribution.

The solvent of the liquid is not particularly limited and can be appropriately selected according to the purpose. Examples of the solvent include, but are not limited to, ion-exchange water, distilled water, pure water, saline, and various organic solvents such as alcohols, mineral oils, and vegetable oils.

When water is used as the solvent, it is preferable that the water contains a wetting agent for preventing evaporation of water and/or a surfactant for reducing surface tension. For the formulation, common materials used for inkjet inks can be used.

Liquid Amount Detector

Preferably, the droplet forming device has a liquid amount detector configured to detect the amount of the liquid in the liquid holder, and the driver is configured to control a vibration isolation waveform based on a detection result of the liquid amount detector.

Even when the natural frequency of the film changes with an increase or decrease of the amount of the liquid in the liquid holder, the liquid amount detector detects the amount of the liquid and inputs a vibration isolation waveform matched to the change of the natural frequency, thereby achieving stable drive efficiency.

The method of detecting the liquid amount with the liquid amount detector is not particularly limited and can be appropriately selected according to the purpose. Examples thereof include, but are not limited to: (1) a method of detecting the amount of a liquid having conductivity by using a plurality of electrodes disposed in the depth direction of the inner wall surface of the liquid holder to measure electrical continuity or resistance value between the electrodes; and (2) a method of calculating the distance to the liquid surface by providing an optical sensor above the liquid holder to emit light to the liquid surface and receive light reflected from the liquid surface and measuring the phase difference between the emitted light and the reflected light.

Particle Number Counter

The particle number counter is configured to count particles contained in the droplet. Preferably, the particle number counter comprises a sensor configured to count the number of particles contained in the droplet after the droplet is discharged and before the droplet lands on a landing target object.

The sensor refers to a device that substitutes mechanical, electromagnetic, thermal, acoustic, or chemical properties of natural phenomena and artifacts, or spatial information or temporal information indicated by them, with a signal of a separate medium that is easy for human or machines to handle by applying some scientific principles.

The particle number counter is not particularly limited and may be appropriately selected according to the purpose. The particle number counter may include a process of observing particles before discharge and a process of counting particles after landing.

The number of particles contained the droplet after discharge of the droplet and before landing of the droplet on the landing target object is preferably counted by observing the particles in the droplet at a time when the droplet is positioned immediately above a well opening of a plate as the landing target object where the droplet is expected to enter.

The plate is not particularly limited, and one having a hole generally used in the field of biotechnology may be used.

The number of wells in the plate is not particularly limited and may be appropriately selected depending on the purpose, and may be either singular or plural.

As a plate having a plurality of wells, a plate in which holes are formed with general number and size in the industry is preferably used, such as that having 24, 96, or 384 wells.

The material of the plate is not particularly limited and may be appropriately selected according to the purpose. For later processes, those having reduced adhesion to the wall surfaces of cells or nucleic acids are preferably used.

The method of observing the particles in the droplet may be, for example, an optically detecting method or an electrically/magnetically detecting.

Other Devices

The other devices are not particular limited and can be appropriately selected according to the purpose. Examples thereof include, but are not limited to, a light emitter, a light receiver, a display, and a controller.

Light Emitter

The light emitter is configured to emit light to the droplets discharged from the droplet discharger.

The light emitter is not particularly limited and can be appropriately selected according to the purpose. Examples of the light emitter include, but are not limited to, a solid-state laser, a semiconductor laser, and a dye laser.

Examples of solid-state lasers include, but are not limited to, YAG laser, ruby laser, and glass laser.

Examples of commercially available products of YAG laser include, but are not limited to, EXPLORER ONE-532-200-KE (manufactured by Spectra-Physics KK).

The spot diameter of the laser is not particularly limited and can be appropriately selected according to the purpose, but is preferably from 100 to 2,000 μm. When the spot diameter is from 100 to 2,000 μm, the probability that the droplet is irradiated with the laser beam is high even when a variation occurs in discharging the droplets, so that a decrease in counting accuracy of the particles in the droplet is advantageously prevented.

Preferably, the light emitted from the light emitter is pulsed light. The accuracy in counting the number of the particles in the droplet can be thereby improved.

The pulse width of the pulsed light is not particularly limited and can be appropriately selected according to the purpose, but is preferably 10 μl is or less, and more preferably 1 μs or less.

The energy per unit pulse is not particularly limited and can be appropriately selected according to the purpose. Although largely depending on the optical system (e.g., whether a condenser is present or not), the energy per unit pulse is preferably 0.1 µJ or more, and more preferably 1 µJ or more.

The light emitter emits light to the droplet in flight. Here, the droplet "in flight" refers to a state from discharge of the droplet to landing of the droplet on the landing target object.

Preferably, the light emitter is capable of emitting light in synchronization with discharge of the droplet. Thus, the droplet discharged from a different position is more reliably irradiated with light.

Here, the synchronization is achieved as the light emitter emits light at the time when the discharged droplet reaches a predetermined position. That is, the light emitter emits light with a delay of a predetermined time period from the discharge of the droplet.

Preferably, the light emitter emits light to only one droplet in flight.

Light Receiver

The light receiver is configured to receive light from the particles irradiated with light.

The light receiver is not particularly limited and may be appropriately selected according to the purpose. Examples of the light receiver include, but are not limited to, a camera having a one-dimensional element or a two-dimensional element. Among these, a camera having a two-dimensional element is preferable. When the light receiver is a camera having a two-dimensional element, it is advantageously easy to obtain not only the luminance value of the emitted light but also the shape on the emitted light receiving surface.

Specific examples of the one-dimensional element include, but are not limited to, a photodiode and a photosensor. Among these, a photomultiplier tube and an avalanche photodiode are preferable. When the one-dimensional element is a photomultiplier tube or an avalanche photodiode, a highly sensitive measurement is possible.

Specific examples of the two-dimensional element include, but are not limited to, a charge coupled device (CCD), a complementary metal oxide semiconductor (CMOS) image sensor, and a gate CCD.

As the light receiver, a camera having a CMOS image sensor is preferable.

Examples of commercially available products of the camera having a CMOS image sensor include, but are not limited to, a highly sensitive camera (pco.edge, sCMOS, manufactured by Tokyo Instruments, Inc.).

In a case in which the droplet in flight contains particles capable of emitting light upon irradiation with light, the light receiver receives fluorescence emitted from the particles that have absorbed the light as excitation light. Since the fluorescence is emitted from the particles in all directions, the light receiver can be disposed at any position where the light emitted from the particles can be received. To improve contrast, the light receiver is preferably disposed on a position where light emitted from the light emitter is not directly incident.

Preferably, two or more light receivers are provided and each light receiver receives light emitted from the particles in different directions. As two or more light receivers are provided, even when one of the light receivers receives the emitted light in an overlapping manner, other one of the light receivers may receive the emitted light in a non-overlapping manner, so that the particles contained in the droplet can be counted at high accuracy based on the emitted light received by the other one of the light receivers.

Since light is emitted in all directions from the particles capable of emitting light upon irradiation with light, two or more light receivers can be disposed at any position where the light emitted in different directions from the particles capable of emitting light upon irradiation with light can be received. Note that three or more light receivers may be disposed at any position where the light emitted in different directions from the particles capable of emitting light upon irradiation with light can be received. The light receivers may have either the same specification or different specifications.

In a case in which the number of light receivers is one, when the droplet in flight contains a plurality of particles capable of emitting light upon irradiation with light, the particle number counter may erroneously detect the number of the particles capable of emitting light upon irradiation with light (i.e., a count error may occur) due to overlapping of the particles capable of emitting light upon irradiation with light with each other. In a case in which two or more light receivers are provided, the influence of overlapping of the particles capable of emitting light upon irradiation with light can be reduced.

One embodiment of the particle number counter to be described later can be implemented by comparing a luminance value or an area value of the particles capable of emitting light upon irradiation with light with a preset threshold value. When two or more light receivers are provided, the occurrence of a count error can be reduced by adopting data indicating the maximum value from among the luminance values or the area values obtained from the light receivers, since the luminance value and the area value both decrease when overlapping of the particles occurs. When a plurality of two-dimensional light receiving elements are provided, the number of particles may be determined by an algorithm for estimating the number of particles based on a plurality of obtained shape data.

The particles irradiated with light emit light in all directions. Therefore, the two or more light receivers are not particularly limited and can be appropriately selected according to the purpose as long as they are disposed at a position where the emitted light can be received. Preferably, the light receivers are disposed such that the angle formed between the light receiving directions thereof is not zero degree. In this case, information is obtained in a state of less overlapping of light emission, which is advantageous.

When the number of light receivers is two, preferably, one of the light receivers is disposed such that the light receiving direction thereof is substantially orthogonal to the light receiving direction of the other one of the light receivers. Thus, among information received by the one of the light receivers and the other one of the light receivers, information in a state of less overlapping of light emission can be selected. Here, "substantially orthogonal" refers to a state in which the angle therebetween ranges from 80 to 100 degrees.

The light receiving directions of the light receivers other than the above-described two light receivers are not particularly limited and can be appropriately selected according to the purpose. When two or more light receivers are disposed on the same plane, it is preferable that the angle formed between the light receiving directions of adjacent light receivers is an angle obtained by equally dividing 360 degrees by the number of light receivers. For example, when three light receivers are disposed on the same plane, it is preferable that the angle formed between the light receiving directions of adjacent light receivers is 120 degrees.

Preferably, the light receiver is arranged such that the light receiving direction thereof is substantially orthogonal to the direction of discharge of the droplets. More preferably, all the light receivers are arranged such that the light receiving directions thereof are substantially orthogonal to the direction of discharge of the droplets. This makes it easy to adjust the position of the light receiver, which is advantageous in that the structure of the droplet forming device is not complicated.

To improve contrast, the light receiver is preferably disposed on a position where light emitted from the light emitter is not directly incident.

Preferably, the light receiver is capable of receiving the emitted light in synchronization with discharge of multiple droplets. Thus, multiple droplets discharged from different positions are irradiated with light emitted from the light emitter, and the light receiver more reliably receives the light emitted from the particles.

Here, the synchronization is achieved as the light receiver receives the emitted light at the time when the discharged multiple droplets are irradiated with light upon reaching a predetermined position and the particles capable of emitting light upon irradiation with light emit light. That is, the light receiver detects the emitted light with a delay of predetermined time periods each from the discharge of the multiple droplets from different positions and from the emission of light by the light emitter.

Display

A display or a speaker may be used as an output device. The display is not particularly limited and well-known ones can be appropriately used. Examples of the display include, but are not limited to, a liquid crystal display and an organic electroluminescent (EL) display.

Controller

A controller controls the overall operation of the droplet forming device. Examples of the controller include, but are not limited to, a computer provided with various software and programs.

The droplet forming device according to an embodiment of the present invention is described in detail below with reference to the drawings.

In each drawing, the same reference numerals are given to the same components, and redundant explanation may be omitted. The number, the position, the shape, and the like of the constituent members are not limited to the embodiment described below, and can be suitably determined.

First Embodiment

Figure 2A:
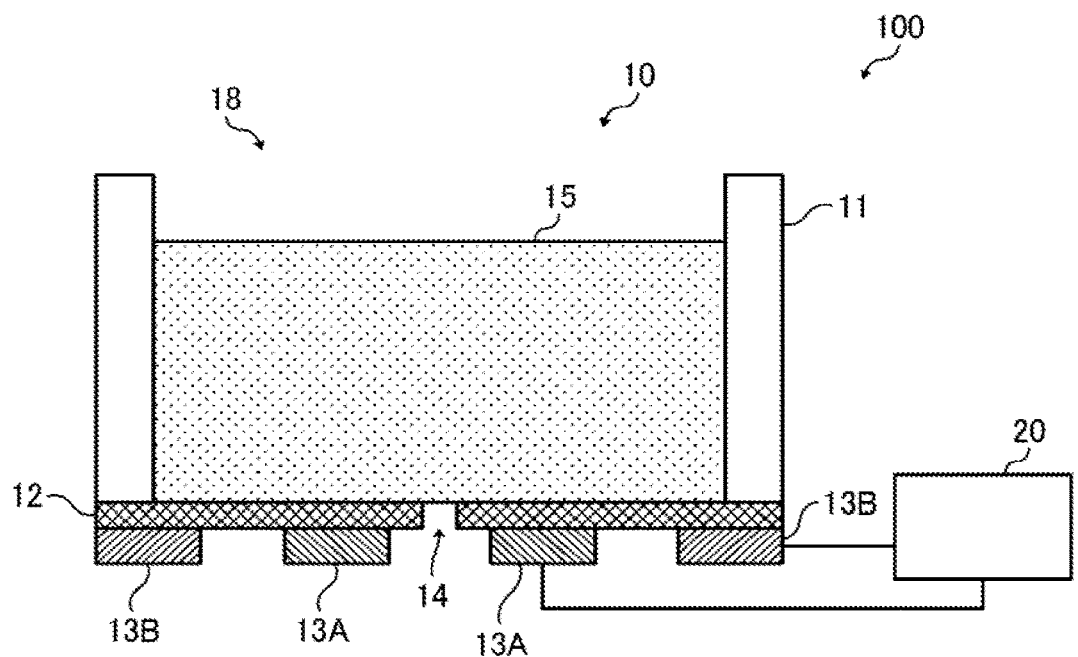
FIG. 2A is a schematic view of a droplet forming device according to a first embodiment of the present invention.
Figure 2B:
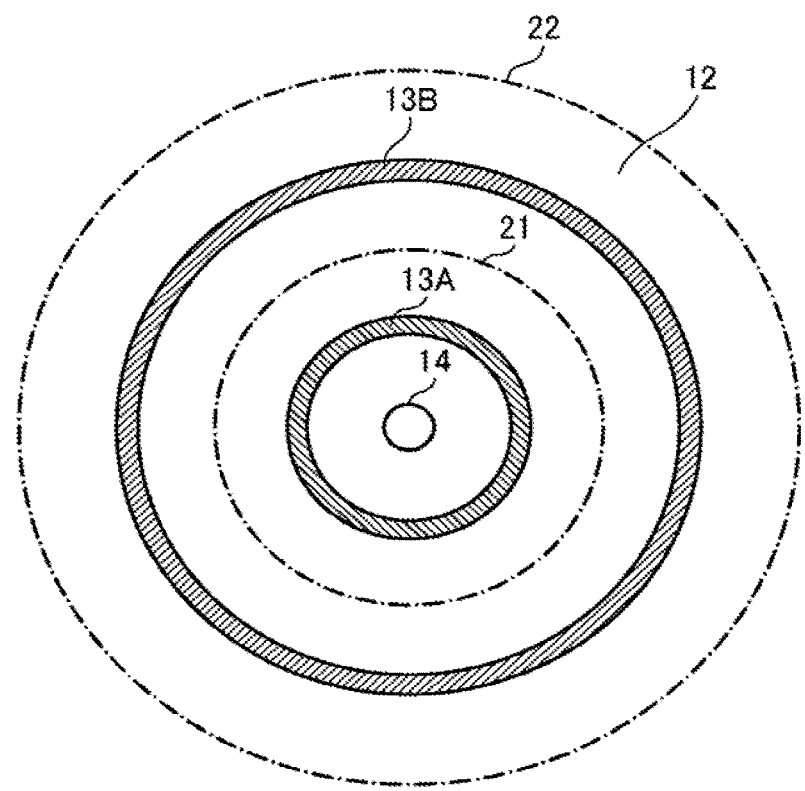
FIG. 2B is a plan view of the film of the droplet forming device illustrated in FIG. 2A viewed from below.

FIG. 2A is a schematic view of the droplet forming device according to a first embodiment of the present invention. FIG. 2B is a plan view of the film of the droplet discharger illustrated in FIG. 2A viewed from below.

A droplet forming device 100 illustrated in FIG. 2A includes a droplet discharger 10 and a driver 20.

The droplet discharger 10 is open-head in the present embodiment. The droplet discharger 10 includes a liquid holder 11 and a film 12 on which a discharge hole 14 is formed. A liquid 15 held in the liquid holder 11 is discharged as droplets from the discharge hole 14 as two vibration generators 13A and 13B apply vibration to the film 12.

The liquid holder 11 holds the liquid 15. Since the droplet discharger 10 is open-head in the present embodiment, an atmospheric opening 18 is provided at an upper portion of the liquid holder 11. Air bubbles mixed in the liquid 15 can be discharged from the atmospheric opening 18.

In the present embodiment, since the droplet discharger 10 is open-head, the two vibration generators 13A and 13B are disposed on the lower surface of the film 12.

Preferably, the vibration generators 13A and 13B are disposed on the film 12 spaced outward by a certain distance from the center of the discharge hole 14, and are arranged in an annular shape with respect to the center of the discharge hole 14, to increase displacement efficiency of the film and shorten the period of residual vibration of the film.

Specifically, referring to FIG. 2B, it is preferable that the two vibration generators 13A and 13B are disposed in each region on the film 12 where the polarity (+/−) of the bending moment differs, i.e., each region on a plus (+) side and a minus (−) side of the film 12 with respect to the bending moment polarity (+/−) conversion line 21 interposed therebetween. This arrangement makes it possible to change the direction of displacement of the film generated by each vibration generator and therefore to individually drive each vibration generator at appropriate timings, thereby increasing displacement efficiency of the film and shortening the period of residual vibration of the film. A reference numeral 22 in FIG. 2B denotes the end portion of the film 12.

Figure 3A:
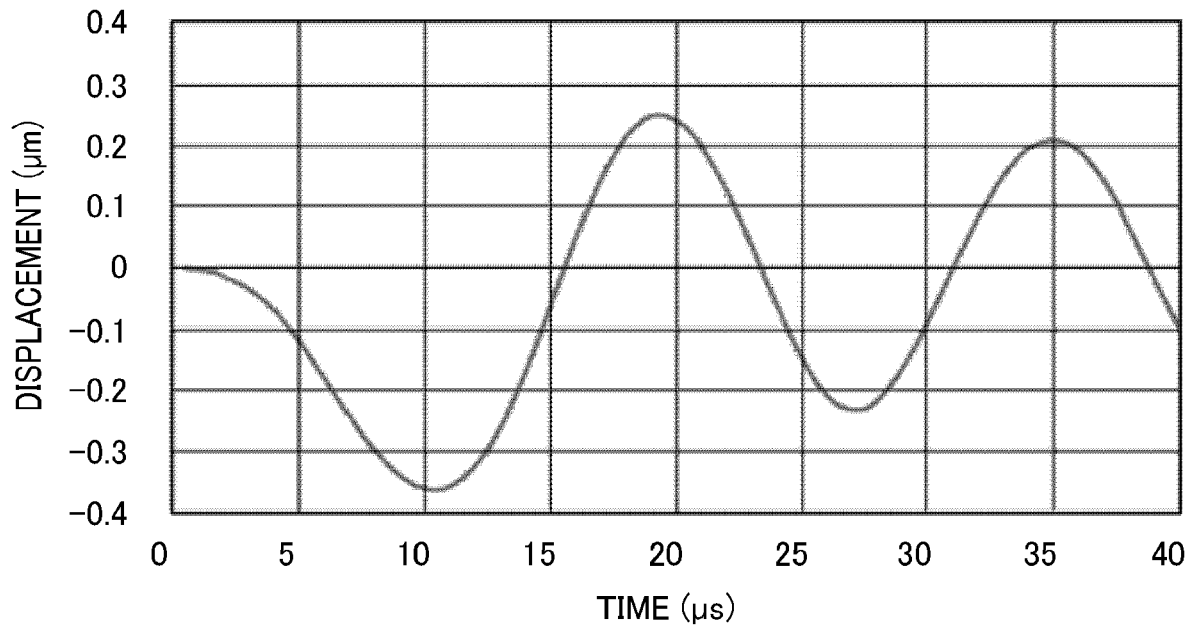
FIG. 3A is a graph showing displacement of the film when a sine wave of a positive voltage is applied to one of the vibration generators.
Figure 3B:
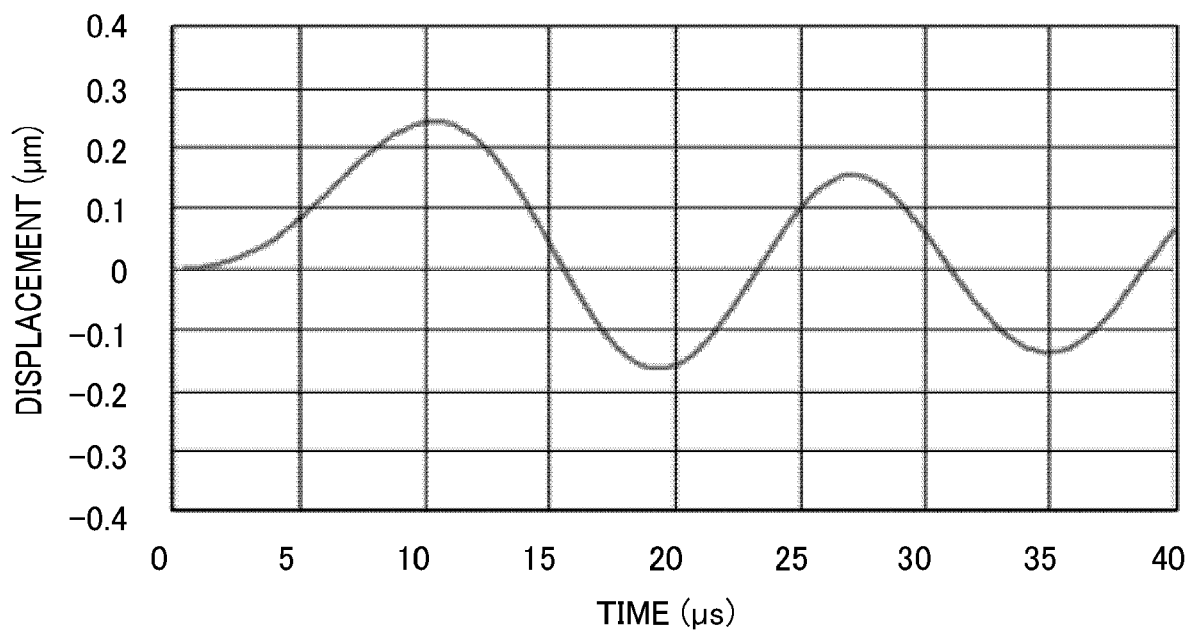
FIG. 3B is a graph showing displacement of the film when a sine wave of a positive voltage is applied to another one of the vibration generators.

When the vibration generator 13B and the vibration generator 13A are arranged as illustrated in FIG. 2B and a sine wave of a positive voltage is applied to the vibration generator 13B, the film displaces in the direction of discharge, i.e., the negative direction of the y axis in the graph as illustrated in FIG. 3A. By contrast, when a sine wave of a positive voltage is applied to the vibration generator 13A, the film displaces in the direction of the liquid holder, i.e., the positive direction of the y axis in the graph as illustrated in FIG. 3B.

Therefore, by individually applying arbitrary driving signals to the two vibration generators 13A and 13B and controlling the displacement state of the film based on the principle of wave superposition, it is possible to increase the amount of displacement (that is one of important factors for forming droplets) immediately after the start of driving and to quickly isolate residual vibration after droplet formation.

Figure 4A:
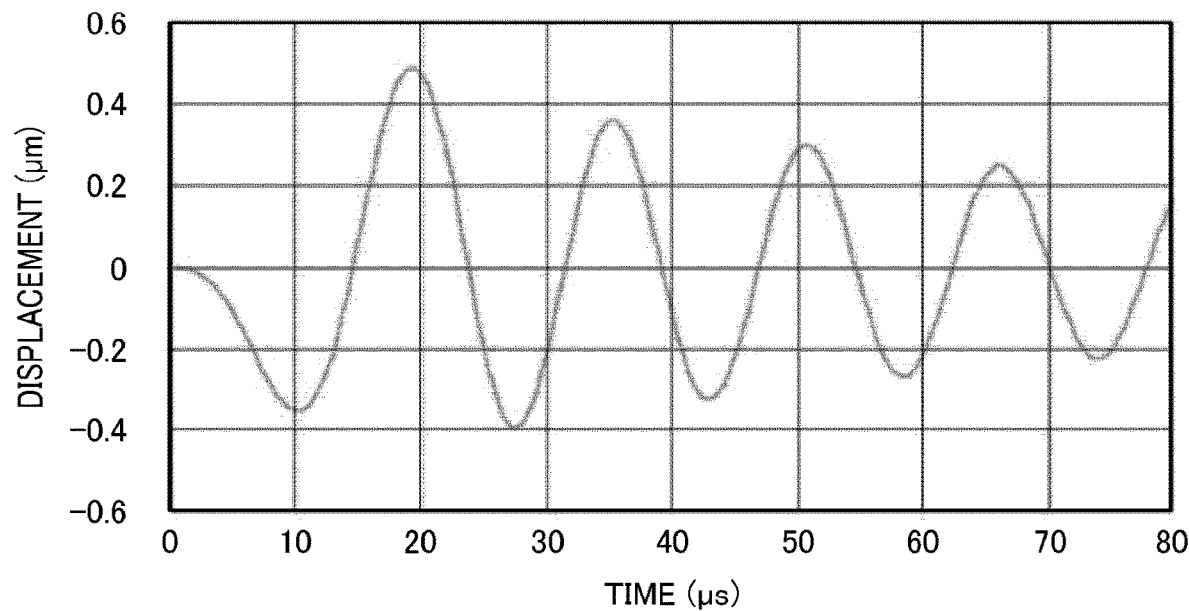
FIG. 4A is a graph showing displacement response of the film when the driving signal applied to each of the vibration generators is so adjusted that displacement peaks of the film generated by the vibration generators are superimposed with each other.
Figure 4B:
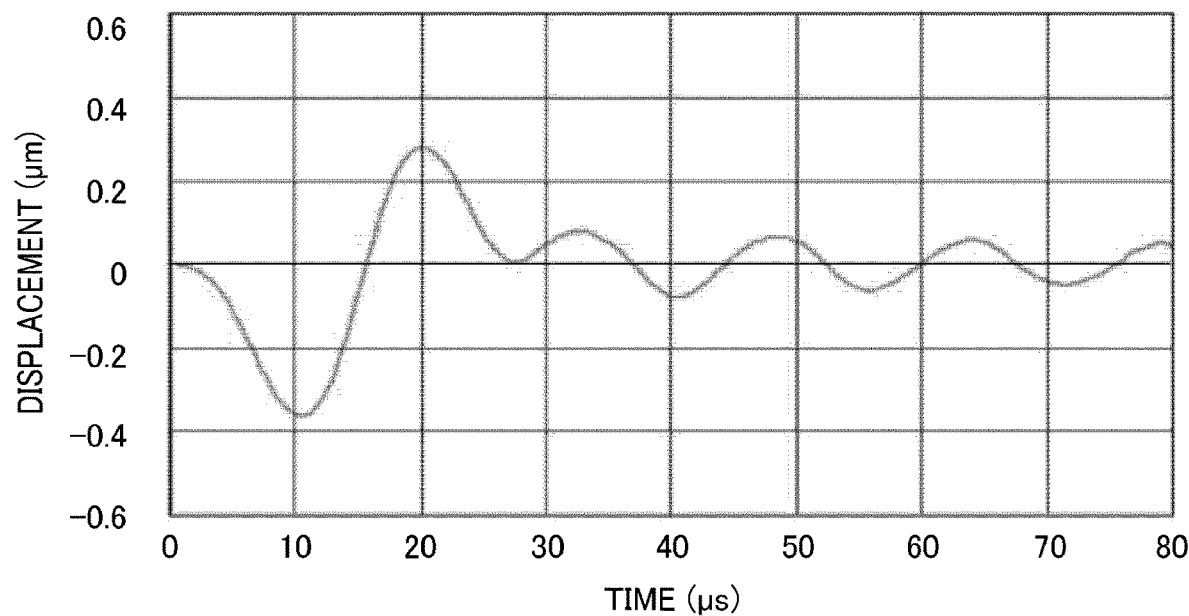
FIG. 4B is a graph showing displacement response of the film when the driving signal applied to each of the vibration generators is so adjusted that displacement peaks of the film generated by the vibration generators are canceled with each other.

FIGS. 4A and 4B are diagrams for explaining specific driving signals for the droplet discharger.

Driving signals applied to the vibration generators 13A and 13B may be so adjusted that displacement peaks of the film 12 generated by the vibration generators 13A and 13B are superimposed with each other. For example, in a case in which the vibration generators 13A and 13B are arranged as illustrated in FIG. 2B, when the applied waveform is set such that the displacement peaks in the displacement responses illustrated in FIGS. 3A and 3B are superimposed and strengthened with each other, the amplitude of the film 12 increases as in the displacement response illustrated in FIG. 4A.

Alternatively, driving signals applied to the vibration generators 13A and 13B may be so adjusted that displacement peaks of the film 12 generated by the vibration generators 13A and 13B are canceled with each other. For example, in a case in which the vibration generators 13A and 13B are arranged as illustrated in FIG. 2B, when the applied waveform is set such that the displacement peaks in the displacement responses illustrated in FIGS. 3A and 3B are superimposed and weakened with each other, residual vibration of the film 12 is reduced as in the displacement response illustrated in FIG. 4B.

Figure 5A:
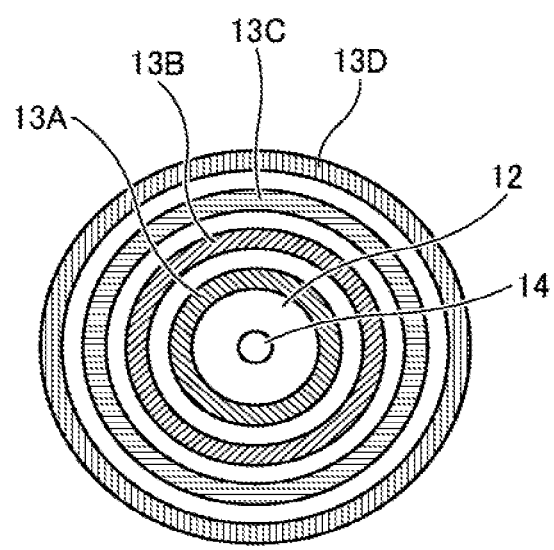
FIG. 5A is a diagram illustrating the shape and arrangement of the vibration generators according to an embodiment of the present invention.
Figure 5B:
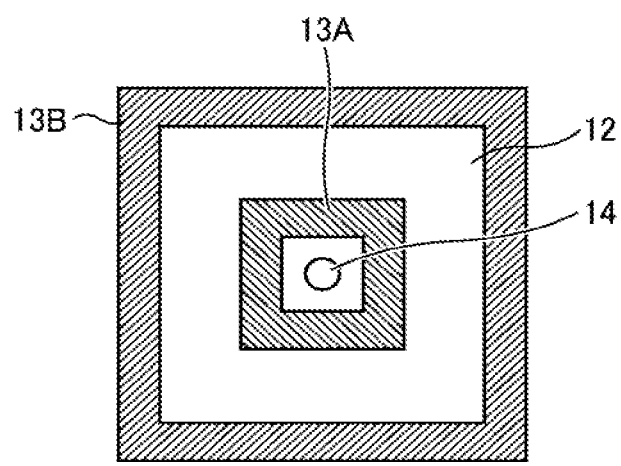
FIG. 5B is a diagram illustrating the shape and arrangement of the vibration generators according to another embodiment of the present invention.
Figure 5C:
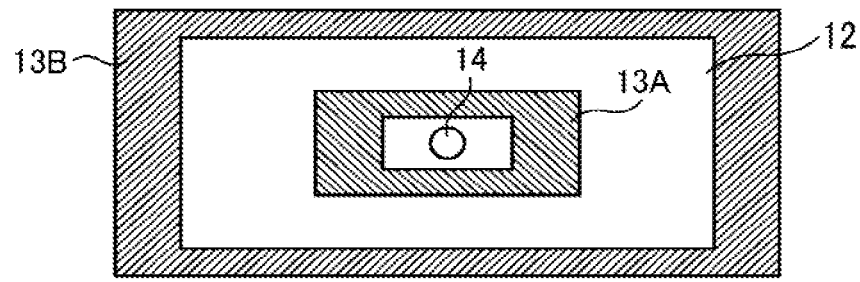
FIG. 5C is a diagram illustrating the shape and arrangement of the vibration generators according to another embodiment of the present invention.
Figure 5D:
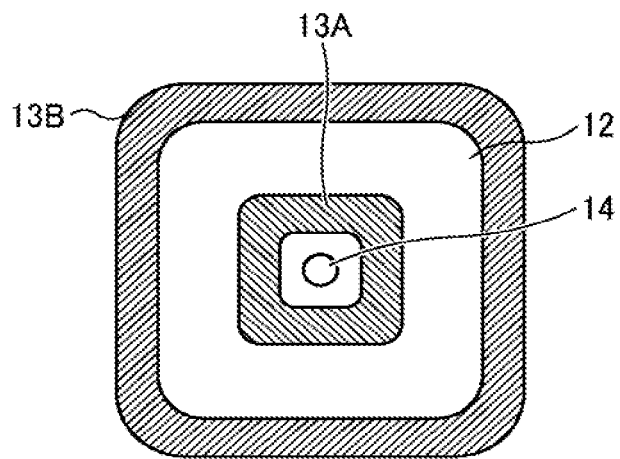
FIG. 5D is a diagram illustrating the shape and arrangement of the vibration generators according to another embodiment of the present invention.
Figure 5E:
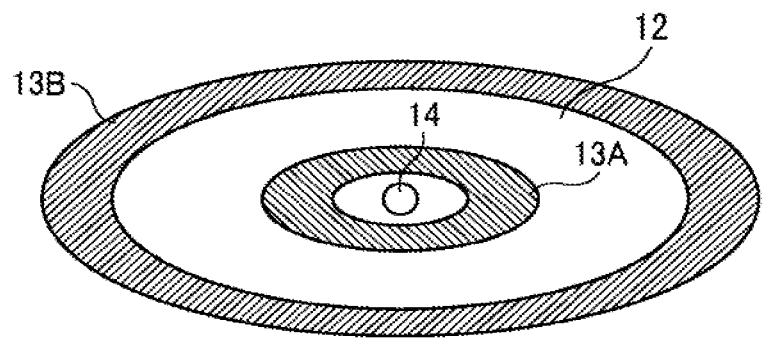
FIG. 5E is a diagram illustrating the shape and arrangement of the vibration generators according to another embodiment of the present invention.

The shape and size of the vibration generators can be designed according to the shape and size of the film 12. Examples of the vibration generators include, but are not limited to, those illustrated in FIGS. 5A to 5E. The shape of the vibration generators may be annular (ring-shaped) as illustrated in FIG. 5A, elliptical as illustrated in FIG. 5E, square-frame-like as illustrated in FIG. 5B, rectangular-frame-like as illustrated in FIG. 5C, or square-frame-like with rounded edges as illustrated in FIG. 5D.

The number of arrangement of the vibration generators is not particularly limited and can be appropriately selected according to the purpose. For simpler preparation processes of the driver and wirings, the preferred number is two. The upper limit of the number of arrangement is not particularly limited, since it is possible to control displacement of the film with higher drive efficiency when the number of arrangement of the vibration generators is increased to 3, 4, or higher.

The two vibration generators 13A and 13B typically comprise a piezoelectric element. As a voltage is applied to the piezoelectric element, compressive stress is applied in the lateral direction of the surface on which FIG. 2B is drawn and the film 12 is deformed.

The material of the piezoelectric element is not particularly limited and may be appropriately selected according to the purpose. Examples thereof include, but are not limited to, various piezoelectric materials such as lead zirconate titanate, bismuth iron oxide, metal niobate, barium titanate, and these materials to which a metal or a different oxide is added.

The two vibration generators 13A and 13B are not limited to piezoelectric elements. For example, a material having a linear expansion coefficient different from that of the film 12 may be attached to the film 12 and heated to deform the film due to the difference in expansion coefficient. In this case, preferably, a heater is formed on the material having a different linear expansion coefficient so that the film can be deformed by heating the heater by application of current.

The driver 20 is capable of selectively applying arbitrary driving signals to the two vibration generators 13A and 13B as discharge waveforms, thereby deforming the film 12 and discharging the liquid 15 held in the liquid holder 11 as droplets.

Different driving signals may be applied to the two vibration generators 13A and 13B to control the phase, amplitude, and cycle of vibration of the film 12 generated by each vibration generators 13A and 13B, thereby increasing the amount of displacement of the film 12 or reducing residual vibration of the film 12 after discharge of droplets. The driving signals applied to the two vibration generators 13A and 13B may all have the same waveform for simplification of generation of driving signals.

Figure 6A:
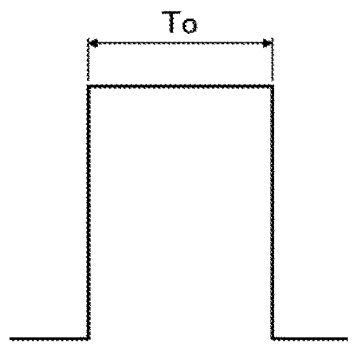
FIG. 6A is a diagram illustrating a waveform of the driving signal applied to the vibration generators.
Figure 6B:
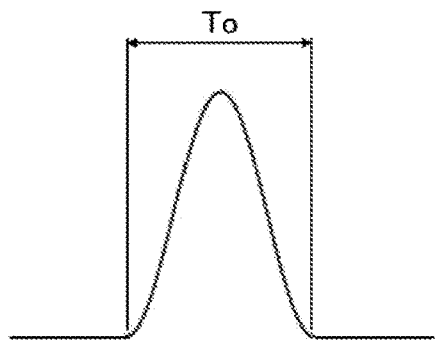
FIG. 6B is a diagram illustrating another waveform of the driving signal applied to the vibration generators.
Figure 6C:
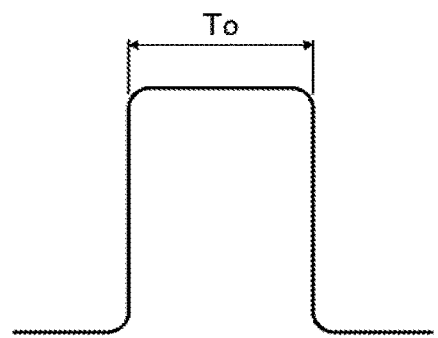
FIG. 6C is a diagram illustrating another waveform of the driving signal applied to the vibration generators.

FIGS. 6A to 6C are diagrams for explaining driving signals applied to the vibration generators of the droplet discharger 10. The driving signal applied to each vibration generator is set to a waveform including the natural vibration cycle To of the film.

The waveform of the driving signal may be, as illustrated in FIGS. 6A to 6C, not only a triangular wave or a sine wave but also a triangular wave having passed a low-pass filter to have a gentle edge.

The amount of the liquid 15 held in the liquid holder 11 is not particularly limited and may be selected according to the purpose, but is preferably from 1 µL to 1 mL. In a case in which the liquid is an expensive liquid such as a cell suspension in which cells are dispersed as particles, it is preferable that droplets can be formed with a small amount of the liquid. More preferably, the amount of the liquid is maintained in a range of from 1 to 50 µL.

The shape of the film 12 may be either circular, elliptical, or polygonal. Regardless of the shape of the film, it is desirable that the vibration generator is disposed inside the inscribed circle region of the film. In the case of arranging the vibration generator on the outer side of the circumference of a circle having a radius r on the film, it is desirable that the vibration generator is arranged such that at least a part thereof is in contact with the film.

The material of the film 12 is not particular limited and may be appropriately selected according to the purpose. However, if the material is too soft, the film is easy to vibrate and difficult to immediately reduce vibration when discharging is suspended. Therefore, a material having a certain degree of hardness is preferable. Generally, metal materials, ceramic materials, and polymer materials having a certain degree of hardness can be used.

Preferably, the discharge hole 14 is formed as a substantially circular through hole at the center of the film 12. The diameter of the discharge hole 14 is not particularly limited and can be appropriately selected according to the purpose, but is preferably from 1 to 200 µm for stabilization of the shape of the discharged droplets.

Second Embodiment

Figure 7:
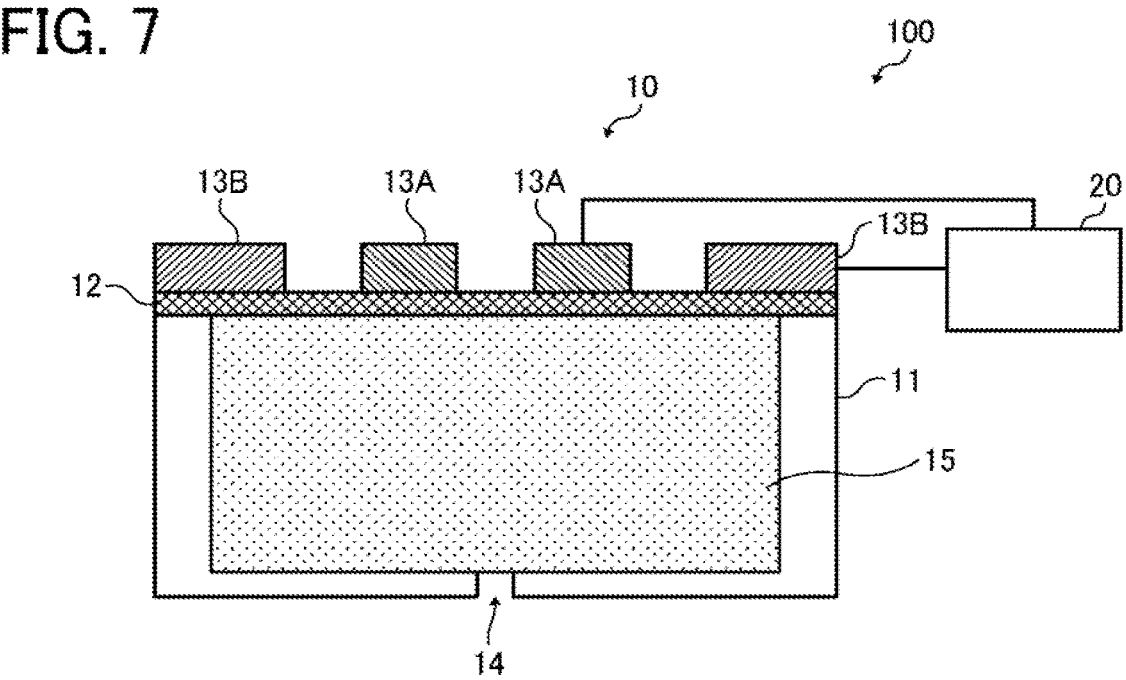
FIG. 7 is a schematic view of a droplet forming device according to a second embodiment of the present invention.

FIG. 7 is a schematic view of the droplet forming device according to a second embodiment of the present invention. In the second embodiment, the same components as those in the embodiments already described are denoted by the same reference numerals, and the description thereof will be omitted.

A droplet forming device 100 illustrated in FIG. 7 includes a droplet discharger 10 and a driver 20.

The droplet discharger 10 is close-head in the present embodiment. The droplet discharger 10 includes a liquid holder 11 having a discharge hole 14 formed on a lower end thereof, and a film 12. A liquid 15 held in the liquid holder 11 is discharged as droplets from the discharge hole 14 as two vibration generators 13A and 13B apply vibration to the film 12.

In the present embodiment, since the droplet discharger 10 is close-head, the two vibration generators 13A and 13B are disposed on the upper surface of the film 12. The film 12 can be vibrated by supplying a driving signal to the two vibration generators 13A and 13B from the driver 20. Thus, droplets can be discharged from the discharge hole 14.

Third Embodiment

Figure 8:
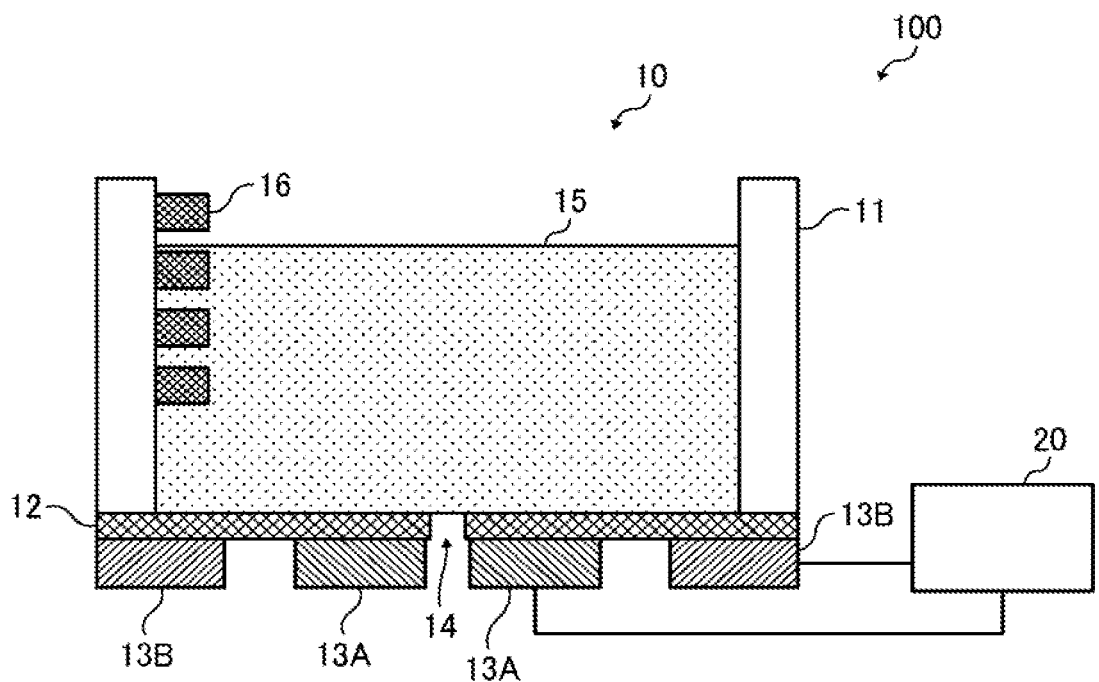
FIG. 8 is a schematic view of a droplet forming device according to a third embodiment of the present invention.

FIG. 8 is a schematic view of the droplet forming device according to a third embodiment of the present invention. In the third embodiment, the same components as those in the embodiments already described are denoted by the same reference numerals, and the description thereof will be omitted.

The droplet forming device 100 according to the third embodiment illustrated in FIG. 8 has the same configuration as the droplet forming device according to the first embodiment except for further including a liquid amount detector capable of detecting the amount of the liquid in the liquid holder.

In the droplet forming device 100 illustrated in FIG. 8, a plurality of electrodes are disposed as a liquid amount detector 16 in the depth direction of the inner wall surface of the liquid holder 11. When the liquid is a liquid having conductivity, the amount of the liquid can be detected by measuring electrical continuity or resistance value between the multiple electrodes.

The driver 20 can be configured to be able to set the vibration isolation waveform based on the detection result of the liquid amount detector 16. For example, the driver 20 can be configured to select an appropriate natural frequency based on a signal related to the liquid amount detected by the liquid amount detector 16 and output a driving signal illustrated in FIGS. 6A to 6C.

Figure 9:
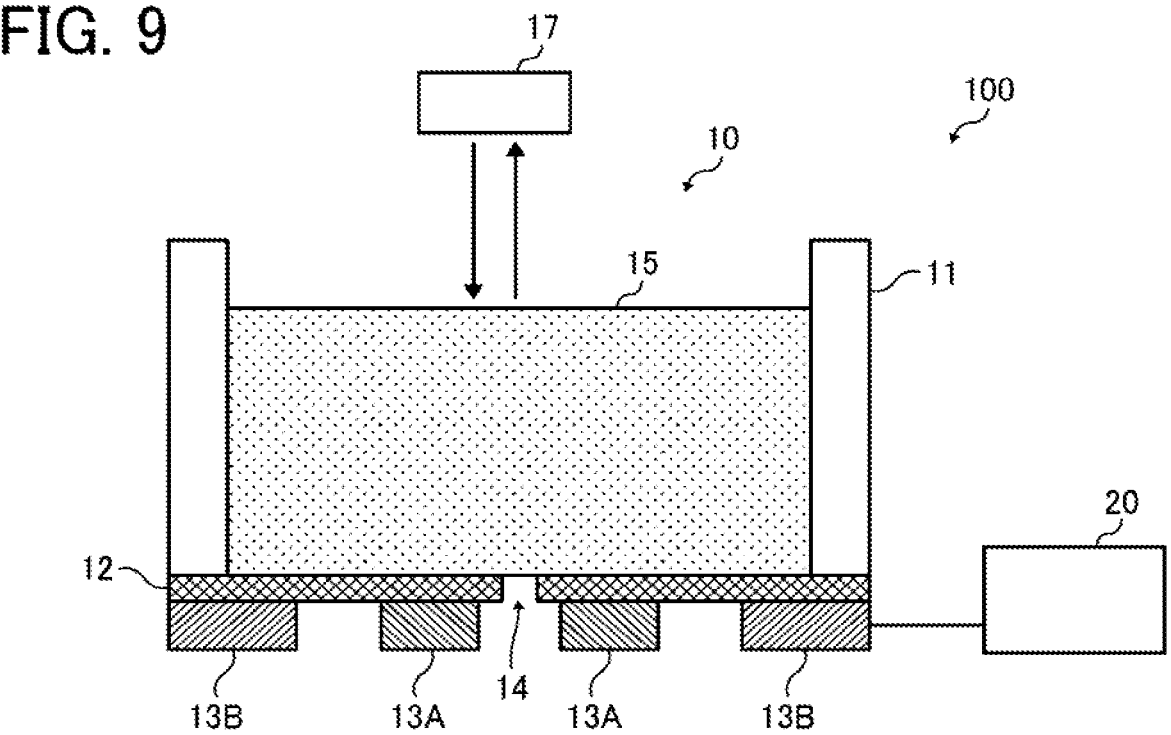
FIG. 9 is a schematic view of another droplet forming device according to the third embodiment of the present invention.

Further, in another example of the droplet forming device 100 according to the third embodiment illustrated in FIG. 9, an optical sensor is provided as a liquid amount detector 17 above the liquid holder 11. Light emitted from the optical sensor is reflected by the liquid surface and the optical sensor receives light reflected from the liquid surface, so that the distance to the liquid surface is calculated by the phase difference between the emitted light and the reflected light.

The liquid amount detector is not limited to those described above, and known various techniques for distance measurement and liquid level detection may be used.

Fourth Embodiment

Figure 10:
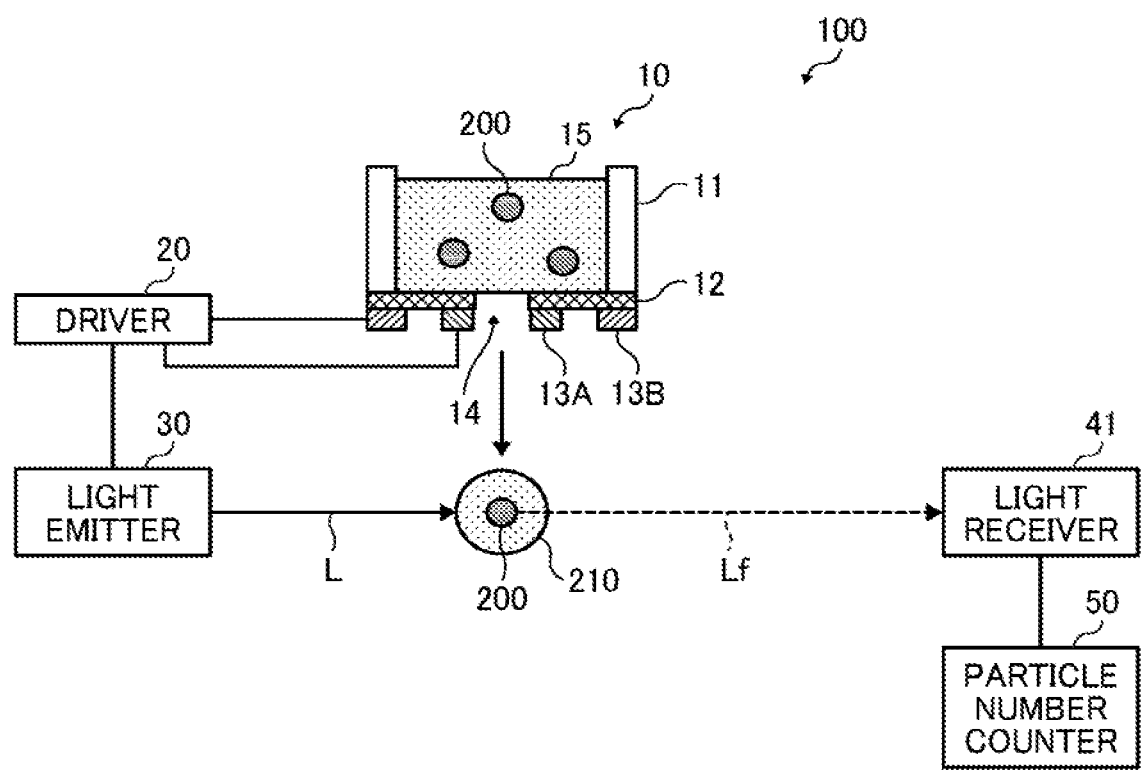
FIG. 10 is a schematic view of another droplet forming device according to a fourth embodiment of the present invention.

FIG. 10 is a schematic view of the droplet forming device according to a fourth embodiment of the present invention. In the fourth embodiment, the same components as those in the embodiments already described are denoted by the same reference numerals, and the description thereof will be omitted.

The droplet forming device 100 according to the fourth embodiment illustrated in FIG. 10 has the same configuration as that illustrated in FIGS. 2A and 2B except for further including a light emitter 30, a light receiver 41, and a particle number counter 50.

The light emitter 30 emits light to a droplet 210 in flight discharged from the discharge hole 14 of the droplet discharger 10. The light emitter 30 is capable of emitting light in synchronization with discharge of the droplet by the droplet discharger 10 (in synchronization with a driving signal supplied from the driver 20 to the droplet discharger 10). Here, the droplet 210 "in flight" refers to a state from discharge of the droplet 210 by the droplet discharger 10 to landing of the droplet 210 on the landing target object.

Here, the synchronization is achieved as the light emitter 30 emits light at the time when the droplet flies to reach a predetermined position and irradiated with light, not at the time when the droplet discharger 10 discharges the droplet (not at the time when the driver 20 supplies a driving signal to the droplet discharger 10). That is, the light emitter 30 emits light with a delay of a predetermined time period from the discharge of the droplet 210 by the droplet discharger 10 (from the supply of the driving signal from the driver 20 to the droplet discharger 10).

Preferably, the light emitter 30 emits light L to only one droplet in flight. When multiple droplets 210 are simultaneously discharged from the discharge hole 14 and light L is simultaneously emitted to the droplets 210, the light emitted from particles 200 contained in the droplets 210 is simultaneously received, so that it becomes difficult to count the number of particles 200 included in each droplet. In order to improve the accuracy in counting the number of particles in the droplet, it is preferable that each droplet is discharged from the discharge hole 14 at a different timing.

Preferably, the light L emitted from the light emitter 30 is pulsed light. For example, a solid-state laser, a semiconductor laser, and a dye laser are suitably used. When the light is pulsed light, the pulse width is preferably 10 μs or less, and more preferably 1 μs or less. The energy per unit pulse is largely depending on the optical system (e.g., whether a condenser is present or not), but is preferably 0.1 μJ or more, and more preferably 1 μJ or more.

In a case in which the droplet in flight contains particles 200, the light receiver 41 receives fluorescence emitted from the particles 200 that have absorbed the light as excitation light. Since the fluorescence is emitted from the particles 200 in all directions, the light receiver 41 can be disposed at any position where the fluorescence can be received. To improve contrast, the light receiver 41 is preferably disposed on a position where light emitted from the light emitter 30 is not directly incident.

Specific examples of the light receiver 41 include, but are not limited to, a one-dimensional element such as a photodiode and a photo sensor. When high sensitivity measurement is required, a photomultiplier tube or an avalanche photodiode is preferably used. Specific examples of the light receiver further include, but are not limited to, a two-dimensional element such as a charge coupled device (CCD), a complementary metal oxide semiconductor (CMOS), and a gate CCD.

Since light Lf emitted from the particles 200 is weaker than light L emitted by the light emitter 30, a filter that attenuates the wavelength range of light may be disposed in front of the light receiver 41 (on the light-receiving surface side). In this case, in the light receiver 41, light with very high contrast can obtain an image of the particles 200. Examples of the filter include, but are not limited to, a notch filter that attenuates a specific wavelength range including the wavelength of light.

The particle number counter 50 detects the number of particles 200 in the droplet (including the case that the number is zero) based on information from the light receiver 41.

The particle number counter 50 may include, for example, a central processing unit (CPU), a read only memory (ROM), a random access memory (RAM), and/or a main memory. In this case, various functions of the particle number counter 50 can be implemented as a program stored in the ROM is read out by the main memory and executed by the CPU. On the other hand, part or all of the particle number counter 50 may be implemented by hardware only. In addition, the particle number counter 50 may be physically configured with a plurality of devices or the like.

For example, the particle number counter 50 can detect the number of particles 200 by comparing the amount of light received by the light receiver 41 with a preset threshold value. In this case, a one-dimensional element or a two-dimensional element may be used as the light receiver 41.

When a two-dimensional element is used as the light receiver 41, the particle number counter 50 may perform an image processing for calculating the luminance value or the area of the particles 200 based on a two-dimensional image obtained from the light receiver 41. In this case, the particle number counter 50 calculates the luminance value or the area value of the particles 200 by image processing, and compares the calculated luminance value or area value with a preset threshold value to detect the number of the particles 200. In the case of using a two-dimensional element, misfiring can be detected by capturing an image of the droplet at a time immediately before receiving the emitted light.

Preferably, the particles 200 are cells, and more preferably cells stained with a fluorescent dye or cells capable of expressing a fluorescent protein. As for these, autofluorescence is received by the light receiver 41, and the particle number counter 50 detects the number of cells contained in the droplet.

Examples of the fluorescent dye include, but are not limited to, Cell Tracker Orange and Cell Tracker Red.

Examples of the fluorescent protein include, but are not limited to, green fluorescent protein (GFP), red fluorescent protein (RFP), and yellow fluorescent protein (YFP).

The droplet forming device and droplet forming method according to some embodiments of the present invention provide sufficient driving force by increasing displacement efficiency of a film and provide high droplet productivity by shortening the period of residual vibration of the film. Therefore, they are suitably used in various fields, particularly suitably used for a dispensing apparatus according to an embodiment of the present invention described below.

Dispensing Apparatus

The dispensing apparatus according to an embodiment of the present invention includes the above-described droplet forming device according to an embodiment of the present invention, preferably further includes a controller, and optionally further includes other devices as necessary.

The dispensing apparatus discharges droplets to a landing target object to cause the droplets to land thereon.

Landing Target Object

The landing target object is a member on which droplets discharged from the droplet discharger of the droplet forming device to land.

The landing target object is not particularly limited in material, shape, size, structure, and the like and can be appropriately selected according to the purpose as long as the discharged droplets can adhere thereto.

The material of the landing target object is not particularly limited and can be appropriately selected according to the purpose. Preferred examples thereof include, but are not limited to, those formed with semiconductor, ceramics, metal, glass, quartz glass, or plastics.

The shape of the landing target object is not particularly limited and can be appropriately selected according to the purpose, but is preferably a board-like shape or a plate-like shape.

The structure of the landing target object is not particularly limited and can be appropriately selected according to the purpose, and may be, for example, a single layer structure or a multiple layer structure.

Examples of the landing target object include, but are not limited to, well plates in which a plurality of recesses are formed and glass plates with no recess. Among these, well plates are preferred.

In the case of using a well plate, when the particle number counter of the droplet forming device determines that the number of particles contained in the droplet is zero, the droplet discharger re-discharges a droplet to the same recess, thereby reliably dispensing the particles into recesses.

The number of recesses provided in the well plate is multiple, preferably 2 or more, more preferably 5 or more, and much more preferably 50 or more.

Controller

The controller is configured to control the relative positional relationship between the droplet discharger and the landing target object, and includes a central processing unit (CPU), a read only memory (ROM), a random access memory (RAM), and a main memory. The controller executes various processing based on a control program for controlling the operation of the entire dispensing apparatus.

Other Devices

The other devices are not particularly limited and may be appropriately selected according to the purpose. Preferably, a recording device, a culturing device, a heating device, a stirring device, and/or a washing device are included.

The dispensing apparatus according to an embodiment of the present invention is equipped with the particle number counter according to an embodiment of the present invention that has an improved detection accuracy of particles contained in the discharged droplets as well as high productivity which can increase the number of discharged droplets per unit time. Therefore, the dispensing apparatus is suitably used for preparation of a tissue, particularly a three-dimensional tissue, which can be widely used in various fields such as regenerative medicine, medicine, cosmetics, and evaluation of safety and efficacy of chemical substances.

The dispensing apparatus according to an embodiment of the present invention is described in detail below with reference to the drawings.

First Embodiment of Dispensing Apparatus

Figure 11:
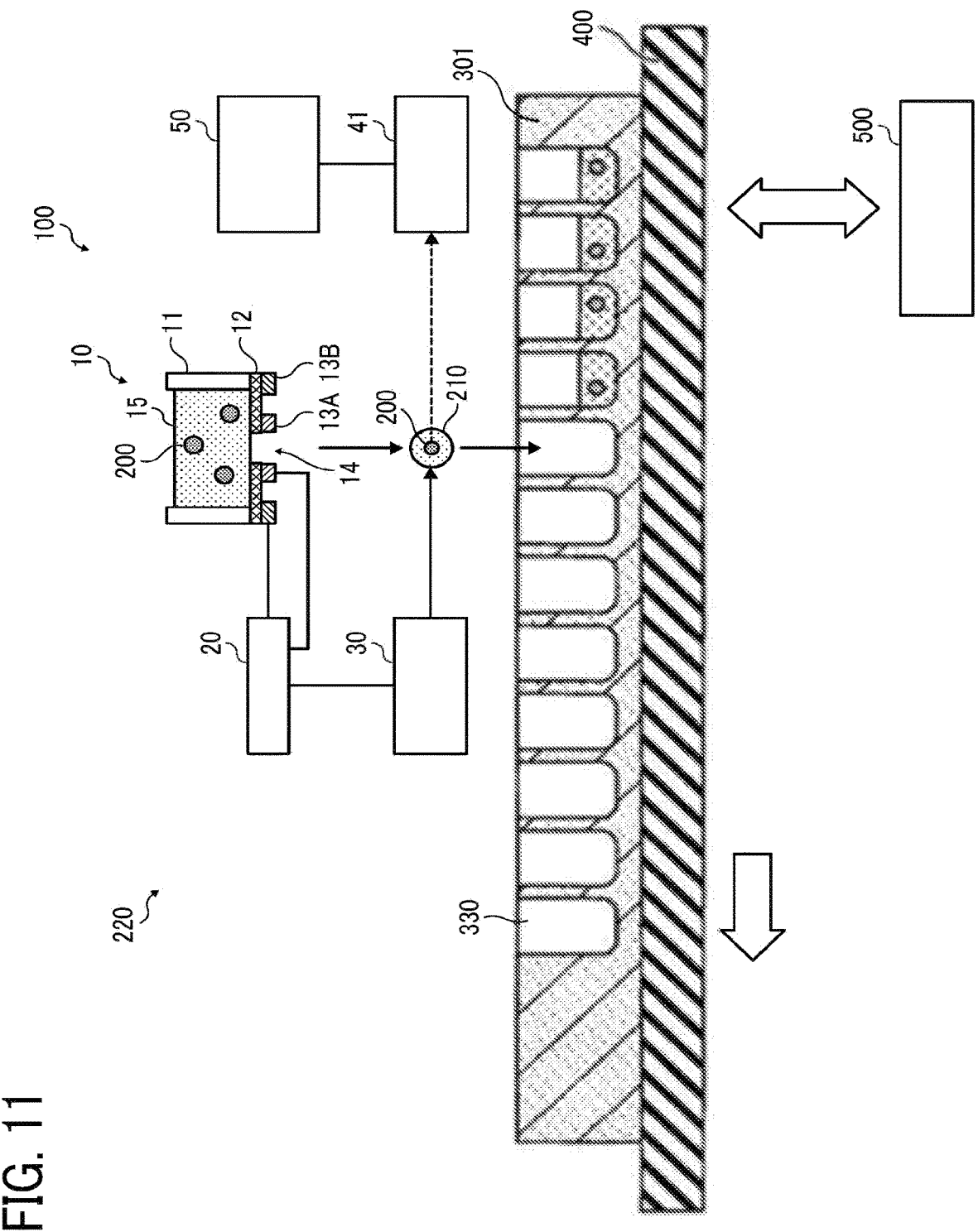
FIG. 11 is a schematic view of a dispensing apparatus according to an embodiment of the present invention.

FIG. 11 is a schematic view of the dispensing apparatus according to a first embodiment. In the first embodiment, the droplet forming device according to an embodiment of the present invention is used as a dispensing apparatus that dispenses particles into recesses of a landing target object. In the dispensing apparatus according to the first embodiment, the same components as those in the embodiments already described are denoted by the same reference numerals, and the description thereof will be omitted.

A dispensing apparatus 220 illustrated in FIG. 11 includes the droplet forming device 100, a landing target object 301, a stage 400, and a controller 500.

The droplet forming device 100 is that according to the fourth embodiment illustrated in FIG. 10.

The landing target object 301 is disposed on the stage 400 configured to be movable. A plurality of recesses (wells) 330 are formed on the landing target object 301, on which droplets 210 discharged from the droplet discharger 10 of the droplet forming device 100 to land.

The controller 500 moves the stage 400 to control the relative positional relationship between the droplet discharger 10 of the droplet forming device 100 and each of the recesses 330. Thus, the droplets 210 containing the particles 200 can be sequentially discharged into each of the recesses 330 from the droplet discharger 10 of the droplet forming device 100. The controller 500 may include, for example, a CPU, a ROM, a RAM, and/or a main memory. In this case, various functions of the controller 500 can be implemented as a program stored in the ROM is read out by the main memory and executed by the CPU. On the other hand, part or all of the controller 500 may be implemented by hardware only. In addition, the controller 500 may be physically configured with a plurality of devices or the like.

Figure 12:
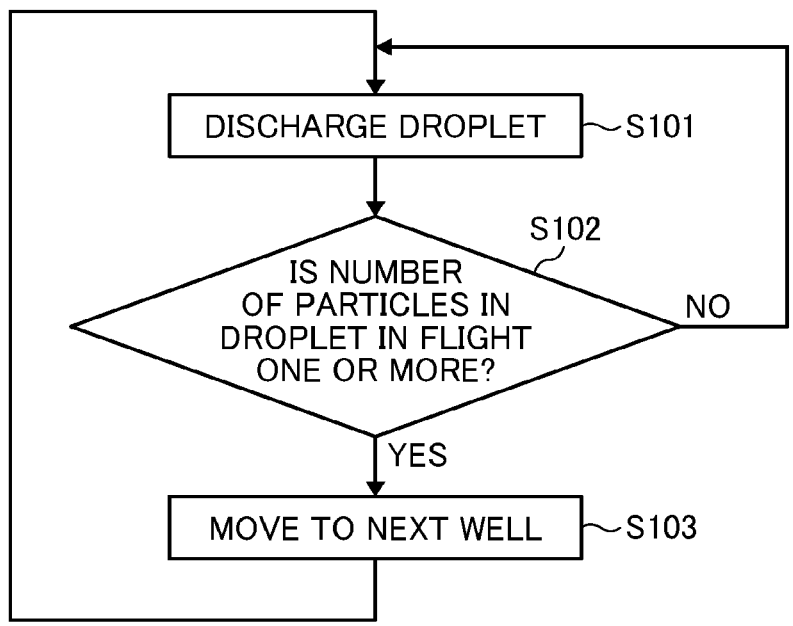
FIG. 12 is a flowchart of an operation of the dispensing apparatus according to an embodiment of the present invention.

FIG. 12 is a flowchart of an operation of the dispensing apparatus according to the first embodiment. First, in step S101, the droplet discharger 10 of the droplet forming device 100 discharges a droplet 210 toward a predetermined recess 330.

Next, in step S102, the particle number counter 50 of the droplet forming device 100 detects the number of particles 200 contained in the droplet 210 in flight and transmits a detection result to the controller 500. If the detection result of the particle number counter 50 is not "one or more" (in the case of zero), the operation of step S101 is repeated.

If the detection result of the particle number counter 50 is "one or more" in step S102, the process proceeds to step S103. In step S103, the controller 500 controls the stage 400 to move the landing target object 301 such that the droplet discharger 10 of the droplet forming device 100 and the next recess 330 come to face each other. The process then transfers to step S101 and repeats the same operation.

Thus, when the number of particles 200 contained in the droplet 210 in flight toward the recess 330 is zero, another droplet 210 is discharged again toward the same recess 330, so that the particles 200 is reliably dispensed into the multiple recesses 330.

Figure 13:
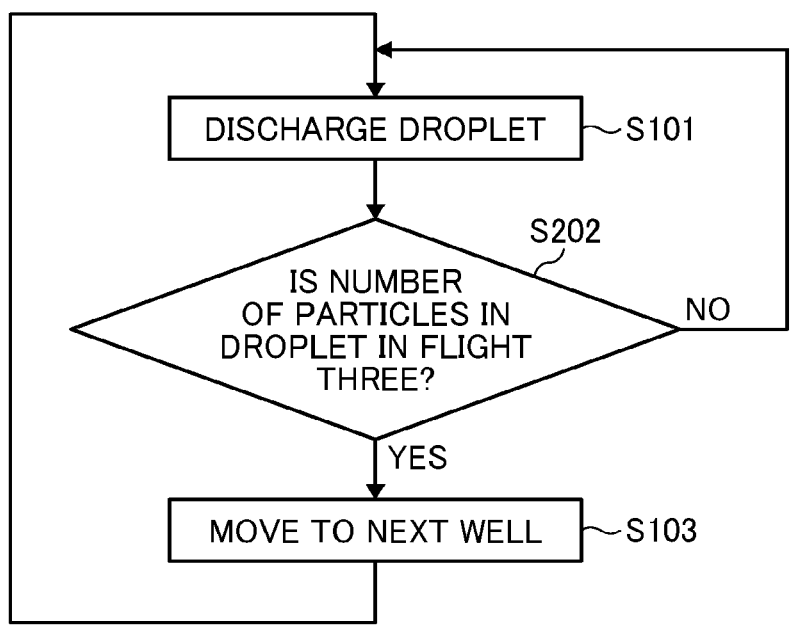
FIG. 13 is a flowchart of another operation of the dispensing apparatus according to an embodiment of the present invention.

It is also possible to detect the number of particles 200 contained in the droplet 210 in flight in the manner illustrated in FIG. 13 instead of based on the presence or absence of particles 200 contained in the droplet 210 in flight.

FIG. 13 is a flowchart of another operation of the dispensing apparatus according to the first embodiment.

In FIG. 13, after step S101 similar to that in FIG. 12 is performed, in step S202, the particle number counter 50 of the droplet forming device 100 detects the number of particles 200 contained in the droplet 210 in flight and transmits a detection result to the controller 500. The operation of step S101 is repeated until the detection result of the particle number counter 50 becomes "three".

Since the detection accuracy of the particle number counter 50 may decrease if the number of particles 200 contained in the droplet 210 increases, the number of particles 200 contained in the droplet 210 discharged at one time is not necessarily set to three. For example, the number of particles 200 contained in the droplet 210 discharged at one time may be set to zero or one. In this case, the operation of step S101 is repeated until the total number of particles 200 contained in the droplet 210 becomes three.

If the detection result of the particle number counter 50 is "three" in step S202, the process proceeds to step S103 similar to that in FIG. 12. The process then transfers to step S101 and repeats the same operation. Thus, it is possible to dispense the particles 200 so that the number of particles 200 in each recess 330 is three.

In the processes illustrated in FIGS. 12 and 13, the function of moving the droplet forming device 100 to a predetermined position along the stage 400 can be included as a program into the controller 500.

Numerous additional modifications and variations are possible in light of the above teachings. It is therefore to be understood that, within the scope of the above teachings, the present disclosure may be practiced otherwise than as specifically described herein. With some embodiments having thus been described, it will be obvious that the same may be varied in many ways. Such variations are not to be regarded as a departure from the scope of the present disclosure and appended claims, and all such modifications are intended to be included within the scope of the present disclosure and appended claims.

The invention claimed is:

1. A droplet forming device, comprising:
a liquid holder configured to hold a liquid;
a film having a discharge hole;
two or more vibration generators configured to vibrate the film; and
a driver configured to selectively apply a separate driving signal to each of the two or more vibration generators to independently drive each of the two or more vibration generators,
wherein one of the two or more vibration generators is disposed in a first region on the film where a polarity of bending moment is positive, and another of the two or more vibration generators is disposed in a second region on the film where the polarity of bending moment is negative.

2. The droplet forming device according to claim 1, wherein the two or more vibration generators are disposed on the film spaced outward by a certain distance from a center of the discharge hole.

3. The droplet forming device according to claim 2, wherein the two or more vibration generators are disposed on the film in an annular shape with respect to the center of the discharge hole.

4. The droplet forming device according to claim 2, wherein the two or more vibration generators are disposed on the film in a frame-like shape with respect to the center of the discharge hole.

5. The droplet forming device according to claim 1,
wherein the film has a circular shape of radius r,
wherein one of the two or more vibration generators is disposed inside a concentric circular region on the film having a radius of approximately (½)r and another one of the two or more vibration generators is disposed outside the concentric circular region.

6. The droplet forming device according to claim 1, wherein each driving signal contains a natural frequency of the film.

7. The droplet forming device according to claim 1, further comprising:
a liquid amount detector configured to detect an amount of the liquid in the liquid holder,
wherein the driver is configured to control a vibration isolation waveform based on a detection result of the liquid amount detector.

8. The droplet forming device according to claim 1, wherein each driving signal applied to the two or more vibration generators is adjusted so that displacement peaks of the film generated by the vibration generators are imposed with each other.

9. The droplet forming device according to claim 1, wherein each driving signal applied to the two or more vibration generators is adjusted so that displacement peaks of residual vibrations of the film generated by the two or more vibration generators cancel each other.

10. The droplet forming device according to claim 1, further comprising:
a particle number counter configured to count a number of particles contained in a droplet discharged from the discharge hole.

11. A droplet forming method comprising:
forming a droplet with the droplet forming device according to claim 1.

12. A dispensing apparatus comprising:
the droplet forming device according to claim 1.

13. The droplet forming device of claim 1, wherein each of the two or more vibration generators is disposed on the film as a closed-loop shape.

14. The droplet forming device of claim 1, wherein a first vibration generator of the two or more vibration generators is disposed on the film so as to completely enclose a second vibration generator of the two or more vibration generators.

15. The droplet forming device of claim 1, wherein each of the two or more vibration generators is disposed on the film in a same shape.

* * * * *